United States Patent [19]

Hoch et al.

[11] Patent Number: 6,043,045

[45] Date of Patent: *Mar. 28, 2000

[54] SCREENING METHODS FOR THE IDENTIFICATION OF NOVEL ANTIBIOTICS

[75] Inventors: James A. Hoch, La Jolla; Shaoming Huang, San Diego, both of Calif.

[73] Assignee: The Scripps Research Institute, La Jolla, Calif.

[ * ] Notice: This patent is subject to a terminal disclaimer.

[21] Appl. No.: 09/043,337

[22] PCT Filed: Sep. 12, 1996

[86] PCT No.: PCT/US96/14652

§ 371 Date: May 29, 1998

§ 102(e) Date: May 29, 1998

[87] PCT Pub. No.: WO97/10358

PCT Pub. Date: Mar. 20, 1997

Related U.S. Application Data

[63] Continuation-in-part of application No. 08/528,737, Sep. 15, 1996, Pat. No. 5,747,276.

[51] Int. Cl.[7] .................................................. C12Q 1/50
[52] U.S. Cl. .................. 435/17; 435/32; 435/23; 435/24; 435/31; 435/7.2; 435/7.21; 435/4; 435/69.2; 435/176; 435/177; 435/968
[58] Field of Search .................. 435/17, 32, 23, 435/24, 31, 7.2, 7.71, 4, 69.2, 176, 177, 968

[56] References Cited

U.S. PATENT DOCUMENTS 5,747,276  5/1998  Hoch et al. ............................... 435/17

OTHER PUBLICATIONS

Burbulys et al; Cell, vol. 64; pp. 545–552, 1991.
Perego et al; J. Bacteriol.; vol. 171, pp. 6187–6196 (1989).
Satola et al; Proc. Natl. Acad. Sci; USA, vol. 88, pp. 4533–4537, (1991).
Strauch et al; Proc. Natl. Acad. Sci, USA, vol. 87, pp. 1801–1805 (1990).
Trach et al; Res. Microbiol.; vol. 142, pp. 815–823, (1991).
Trach et al; Molec. Microbiol; vol. 8, pp. 69–79, (1993).

*Primary Examiner*—Louise N. Leary
*Attorney, Agent, or Firm*—Thomas Fitting; Emily Holmes

[57] ABSTRACT

The present invention relates to screening methods for the identification of compounds and compositions useful as novel antibiotics and antibacterial agents. In particular, the present invention relates to methods utilizing two-component regulatory switches which includes regulatory switches comprising a prokaryotic enzyme. Histidine protein kinase is a regulatory switch that is activated to autophosphorylate by a signal transduction mechanism. The invention also relates to methods of identifying inhibitors of enzyme activity particularly in bacterial cells. A high-throughput assay system useful in the large-scale screening of protein kinase inhibitors is also provided. The invention further provides the phosphorylation of SpoOF including a histidine.

38 Claims, 4 Drawing Sheets

SCREENING METHODS FOR THE IDENTIFICATION OF NOVEL ANTIBIOTICS

This application is an International 371 of PCT/US96/14652 filed Sep. 12, 1996 and a continuation-in-part of Ser. No. 08/528,737 filed Sep. 15, 1996 U.S. Pat. No. 5,747,276.

TECHNICAL FIELD

The present invention relates to screening methods for the identification of compounds and compositions useful as novel antibiotics, antibacterial agents, and inhibitors of prokaryotic enzyme activity. The invention also discloses a high-throughput assay system useful in the large-scale screening of protein kinase inhibitors and related methods.

BACKGROUND OF THE INVENTION

Antimicrobial therapy has focussed on antibiotics that affect processes unique to bacteria, such as compositions that affect enzymes and components of the cell wall (e.g., penicillin), and prokaryotic ribosome inhibitors (e.g., streptomycin). To a lesser extent, antibiotic therapy has also exploited structural and catalytic differences between enzymes common to prokaryotes and eukaryotes.

Antimicrobial or antibiotic therapy is dependent upon the discovery of biochemical systems that are unique to bacteria and which can be safely inhibited—i.e., systems which can be inhibited without producing detrimental effects or undesired side effects in or upon the individual receiving such therapy. Further, it has been observed that antibiotic resistance increases in pathogen populations due to recruitment of resistance enzymes from the microbial gene pool, partially as a result of antibiotic overuse or misuse. As resistance develops, it has become increasingly difficult to identify unique biochemical pathways which may be inhibited in bacteria, which are not also represented in the cells of higher organisms, including man.

Therefore, one goal of the present disclosure is the revelation of a new, apparently ubiquitous biochemical and regulatory system unique to bacteria, which may be exploited for antimicrobial therapy. Unique regulatory proteins are described herein which are absent from eukaryotic cells and could provide novel targets for antimicrobial therapy.

One exemplary "target" regulatory system involves bacterial protein kinases. Histidine protein kinase plays an important role in bacterial signal transduction. Typically, histidine protein kinase activity is assayed via a two-step procedure including a phosphorylation reaction in the presence of [γ-$^{32}$P]ATP followed by SDS-PAGE and autoradiography analysis. Application of this method in large-scale screening for histidine protein kinase inhibitor is limited, however, largely because of the need to use SDS-PAGE.

The regulation of biological activities of proteins by reversible phosphorylation plays an important role in control of cellular response to extracellular stimuli in both prokaryotic and eukaryotic organisms. Phosphorylation cascades mediated by bacterial two-component systems provide a conserved mechanism for coordinate regulation in response to signal input. In bacteria, diverse processes such as chemotaxis (Hess, et al., *PNAS USA* 84: 7609–7613 (1987); Wylie, et al., *Biochem. Biophys. Res. Commun.* 151: 891–896 (1988); Hess, et al., *Cell* 53: 79–87 (1988)), nitrogen starvation (Ninfa and Magasanik, *PNAS USA* 83: 5909–5913 (1986); Keener and Kotsu, *PNAS USA* 85 4976–4980 (1988); Weiss and Magasanik, *PNAS USA* 85: 8919–8923 (1988)), osmotic regulation (Aiba, et al.,*J. Biol. Chem.* 264: 8563–8567 (1989); Forst, et al., *PNAS USA* 86: 6052–6056 (1989); Igo, et al., *Genes & Dev.* 3: 589–605 (1989)), sporulation (Perego, et al., *J. Bacteriol.* 171: 6187–6196 (1989)), and certain types of antibiotic resistance (Christopher, *Science* 261: 308–309 (1993); Guenzi, et al., *Mol. Microbiol.* 12: 505–515 (1994)) are regulated by a two-component system.

In general, two-component systems comprise a sensor protein (usually a histidine protein kinase) and a response regulator protein. The histidine protein kinase undergoes ATP-dependent autophosphorylation on a histidine residue in response to a stimulus. The phosphorylated sensor protein then transfers the phosphor group to an aspartyl residue of the response regulator protein, which protein either acts as a transcriptional regulator or interacts with another protein.

Inhibition of either the autophosphorylation or the subsequent phosphor-transfer by special inhibitors of the two-component system would interrupt the signal transduction pathway, thereby providing a means to interfere with a particular cellular process. Inhibitors specific to the bacterial two-component system are of particular importance in the development of new antibacterial or antibiotic agents.

An efficient assay system is necessary for large-scale screening of inhibitors of the two-component system. The conventional in vitro assay of the two-component system involves a phosphorylation reaction of histidine protein kinase and its substrate in the presence of [γ-$^{32}$P]ATP. The histidine protein kinase, the response regulator protein, and unincorporated [γ-$^{32}$P]ATP are then separated by SDS-PAGE followed by autoradiographic analysis (Burbulys, et al., *Cell* 64: 544–552 (1991)). Although this conventional assay provides a sensitive measurement of histidine protein kinase activity, the throughput of the assay is very limited due to the SDS-PAGE step. Other separation techniques, such as trichloroacetic acid precipitation and HPLC are not suitable for the two-component system because of the instability of aspartyl phosphate (Burbulys, et al., Id. (1991)). Therefore, the assay systems and methods disclosed herein are particularly useful and overcome the deficiencies of other available methods.

An efficient assay system for histidine protein kinase has now been developed in which the substrate is immobilized onto Ni-resin via a six-histidine tag (or linker). In this assay system, the separation of the substrate from the kinase and [γ-$^{32}$P]ATP is achieved by removal of the reaction mixture from the resin, and the extent of phosphorylation of the substrate is then determined by measuring the radioactivity remaining in the resin.

The data presented herein demonstrate a good and highly reproducible correlation between kinase activity, as measured by the extent of phosphorylation of the substrate and the radioactivity remaining on the resin. This assay system has been adapted into a high throughput screening assay using an automated liquid handling system and 96-well filter plates. This has made it possible to process in excess of six 96-well plates per operator per day.

The within-disclosed high throughput assay for histidine protein kinase is particularly useful for inhibitor screening purposes. An assay system for histidine protein kinase activity without SDS-PAGE separation or acid precipitation is also described. *Bacillus subtilis* KinA (histidine protein kinase) and SpoOF (cognate response regulator) are used as kinase and substrate, respectively, in the within-described assays. It should be appreciated, however, that the disclosed assay systems can also be applied to other protein kinases and their substrates. Kinetic features of the within-disclosed assays and the adaptation of an assay system into a high throughput assay for histidine protein kinases are also presented herein.

BRIEF SUMMARY OF THE INVENTION

Antimicrobial antibiotics designed to intercalate with two-component regulatory switches and inhibit their functioning demonstrate several inherent advantages. In particular, the target of such an antibiotic is distinctly different from that sought by other antibiotic methodologies. Additionally, since two-component regulatory systems are unique to prokaryotes, there should be little, if any, interference with the biochemical mechanisms of the host organism. Moreover, there is more than one target for such antibiotics within each bacterial genus (and species), as there are at least a dozen distinct, yet structurally similar, regulatory systems within bacteria which utilize two-component controlling switches of this type. Thus, resistance by intrinsic target modification is far less likely than with "conventional" antibiotics.

Essential bacterial processes which may be inhibited by blocking regulatory switches include processes contributing to the virulence of various bacteria toward their hosts; for example, the prevention of the secretion of certain exoenzymes may limit the formation of accessory virulence factors such as hemolysins. The considerable potential implicit in this novel approach is based on our observation that the preliminary established structures of the conserved domains show a definite homology for the phospho-accepting regions of the regulatory proteins, suggesting that all of the molecules contain a roughly identical structure. This implies that antibiotics directed toward one target may have a wide—or possibly infinite—spectrum of activity.

Therefore, in one embodiment, the present invention contemplates methods of identifying useful therapeutic agents via the utilization of the elements of a two-component regulatory pathway or "switch". In one variation, a useful method comprises admixing a composition or compound with predetermined (or effective) amounts of a prokaryotic enzyme, a secondary messenger, and a high-energy phosphate source; allowing the admixture to incubate for a predetermined period of time; and examining the admixture after incubation in order to determine the effect of the agent upon the activity of the enzyme. In various embodiments, the enzyme comprises a histidine protein kinase; the phosphate source is ATP or GTP; and the kinase is kinase A. In still other embodiments, the secondary messenger comprises a molecule capable of transferring one or more phosphate groups. In one variation, the molecule comprises a protein; in another embodiment, the protein is SpoOF.

Therefore, in one embodiment, the present invention discloses an improved assay method for use in identifying novel antibiotic, antibacterial, or antimicrobial agents, comprising the following steps: (a) affixing a substrate onto a solid support; (b) admixing the solid support-affixed substrate with a sensor protein and a test sample; (c) allowing the admixture to incubate for a predetermined period of time; (d) separating the solid support from the remainder of the admixture; and (e) examining the solid support to determine whether a reaction product is present, thereby determining the therapeutic potential of the test sample.

In one variation of the foregoing method, the invention contemplates that the sensor protein is an enzyme or a catalytically active portion thereof. In another variation, the enzyme is a kinase enzyme or an enzymatically active polypeptide portion thereof. In one particular embodiment, the kinase is histidine protein kinase.

In another variation, the admixture further includes a high-energy phosphate source. For example, the high-energy phosphate source may be ATP or GTP. In various embodiments, the high-energy phosphate source is labeled.

Still another embodiment contemplates that the substrate comprises a bacterial protein or polypeptide molecule. In one variation, the substrate comprises a bacterial SpoOF protein or a polypeptide portion thereof. In another, the substrate further comprises a linker. One set of exemplary linkers comprises one or more histidine residues.

Another embodiment of the invention provides that the solid support comprises a resin. In one preferred embodiment, the resin is a nickel-conjugated exchange resin (Ni-resin).

In an alternative embodiment, the present invention discloses an assay method for identifying antibiotic, antibacterial or antimicrobial agents, comprising (a) affixing a substrate onto a solid support; (b) admixing the solid phase-affixed substrate with a sensor protein, a high-energy phosphate source, and a test sample; (c) allowing the admixture to incubate for a predetermined period of time; and (d) examining the admixture after the incubation in order to determine the effect of the test sample upon the activity of the sensor protein. In one variation, the examining step comprises removing the reaction admixture from the solid support and determining the amount of radioactivity remaining on the solid support, thereby determining the effect, if any, of the test sample on the activity of the sensor protein.

In one alternative embodiment of the within-described method, the high-energy phosphate source is ATP. In another variation, the high-energy phosphate source is GTP.

In various embodiments, the sensor protein comprises a bacterial or microbial protein or polypeptide molecule; in one variation, the sensor protein comprises an enzyme. In various preferred embodiments, the sensor protein comprises microbial or bacterial enzymes or catalytically active portions thereof.

A sensor protein need not, however, consist solely of an enzyme or a catalytically active portion thereof; a sensor protein may comprise any protein or polypeptide molecule. For example, a sensor protein of the present invention may comprise a protein or polypeptide derived from a bacterial or microbial organism. A sensor protein may also comprise a protein or polypeptide that is capable of undergoing a modification or change—e.g., a chemical modification or change—that effectively signals the action of one molecule upon another. Thus, in one exemplary embodiment, a sensor protein comprises a protein or polypeptide molecule which is capable of undergoing phosphorylation.

In one embodiment of the present invention, the sensor protein is a kinase enzyme or a polypeptide portion thereof. In another embodiment, the sensor protein is a protein or polypeptide exhibiting homology in sequence to a protein kinase or polypeptide portion thereof. In another preferred variation, the sensor protein is a histidine protein kinase.

In various embodiments of the disclosed invention, the substrate preferably comprises a protein or polypeptide molecule which may be acted upon by the sensor protein. Thus, in one exemplary embodiment—e.g., when the sensor protein comprises an enzyme—the substrate comprises a protein or polypeptide molecule which is recognized by said enzyme.

In one disclosed embodiment, the substrate comprises a SpoOF protein or a polypeptide portion thereof. In another embodiment, the substrate further includes a linker or "tag"—e.g., one or more histidine residues—attached to one of its termini. In a preferred embodiment, the linker or tag is attached to the N-terminus of the substrate.

One embodiment of the invention discloses that the solid support comprises a gel or a resin. In one preferred variation, the solid support is a resin, more preferably, a Ni-resin. In other preferred embodiments of the disclosed assay methods, either the enzyme, the substrate, or a specific binding agent is labeled. Alternatively, two or more of the assay components may be labeled, albeit it is preferable that different components have different labels, to facilitate easier identification. A variety of labels are available and recognized in the art, including radioactive labels, immunoreactive labels (e.g. immunoglobulin molecules or immunologically active portions thereof), chromogenic labels, fluorescent labels, and the like.

The invention further discloses a method for identifying novel antibiotic, antibacterial or antimicrobial agents, comprising the following steps: (a) admixing a substrate with a kinase enzyme, a high-energy phosphate source, and a test sample; (b) allowing the admixture to incubate for a predetermined period of time; (c) separating any reaction product formed in step b from the remainder of the admixture; and (d) ascertaining the amount of reaction product formed, thereby determining the therapeutic potential of the test sample. In one variation, the substrate or the enzyme is labeled; in another variation, both are labeled. In still another variation, the determining step (step d) comprises using a labeled antibody which forms a labeled immunocomplex with a substrate or an enzyme, and then quantitating the amount of labeled immunocomplex formed. The invention also contemplates that in any of the foregoing methods, the label may comprise a fluorescent label, a radioactive label, biotin, and the like, to name a few examples.

In another embodiment of the invention, the substrate is preferably affixed to a solid support. In one variation, the solid support comprises a resin. In a preferred variation, the resin is a nickel-conjugated exchange resin (Ni-resin).

Another embodiment contemplates that the high-energy phosphate source is ATP or GTP. In still another variation, the enzyme comprises a kinase enzyme or a polypeptide having an amino acid residue sequence corresponding to that of a sequential subset of the amino acid residue sequence of the enzyme. In one embodiment, the kinase is histidine protein kinase. In yet another embodiment, the substrate comprises a bacterial protein or polypeptide molecule.

The present invention also discloses a variety of assay systems. For example, one disclosed embodiment describes a high-throughput assay system comprising, in separate containers, (a) a substrate affixed to a solid support; (b) a sensor protein; and (c) a high-energy phosphate source, each in an amount sufficient to conduct at least one assay.

In one variation of the within-disclosed assay system, either the substrate, the sensor protein, or the phosphate source is labeled. In various preferred embodiments, the label comprises a radioactive label or "tag". In other preferred embodiments, the label is a fluorescent molecule, or it comprises an enzyme, an immunoglobulin molecule or an immunologically active portion thereof (e.g., an active site-containing portion).

In assay systems of the present invention, a high-energy phosphate source may also be included. In one variation, the high-energy phosphate source is ATP. In another variation, the high-energy phosphate source is GTP.

In various embodiments, the sensor protein comprises a bacterial or microbial protein or polypeptide molecule; more preferably, the sensor protein comprises a microbial or bacterial enzyme. In one preferred embodiment, the sensor protein is a kinase enzyme. In another preferred variation, the sensor protein is a histidine protein kinase.

In yet another variation, the substrate comprises a SpoOF protein or a polypeptide portion thereof. In another embodiment, the substrate further includes one or more histidine residues attached to its N-terminus.

One embodiment of the invention discloses that the solid support comprises a gel or a resin. In one preferred variation, the solid support is a resin, more preferably, a Ni-resin. In other preferred embodiments of the disclosed assay methods, either the enzyme, the substrate, or a specific binding agent is labeled. Alternatively, two or more of the assay components may be labeled, albeit it is preferable that different components have different labels, to facilitate easier identification. A variety of labels are available and recognized in the art, including radioactive labels, immunoreactive labels (e.g. immunoglobulin molecules or immunologically active portions thereof), chromogenic labels, fluorescent labels, and the like.

In a further variation, the system further includes a solid support to which one or more of the reagents may be affixed. Said one or more reagents may be provided already-affixed to such a solid support; alternatively, they may be affixed to the solid support at a later time by the user of the system or kit. In one disclosed embodiment, the solid support comprises a resin. In a preferred variation, the resin is a Ni-resin.

The present invention also discloses assay systems including one or more substrate molecules. In various preferred embodiments, the substrate comprises bacterial protein or polypeptide molecules. In one variation, such a protein or polypeptide is derived from B. subtilis. In other variations, substrate proteins or polypeptides are derived from other bacterial or fungal species.

In one embodiment, an assay system of the present invention includes a substrate comprising a SpoOF protein or a polypeptide portion thereof. In another variation, the substrate further includes one or more histidine residues attached to its N-terminus.

More particularly, the invention discloses a high-throughput assay system or kit comprising the following reagents: (a) a substrate affixed to a solid support; (b) a sensor protein; and (c) a high-energy phosphate source, each in an amount sufficient to conduct at least one assay. In one variation, one or more of the reagents is labeled. In another variation, each of the reagents is in a separate container. The containers may conveniently be included within a package or kit. In various preferred embodiments, the package or kit may also include instructions for use of the reagents.

Another embodiment discloses that the sensor protein comprises an enzyme or a catalytically active portion thereof. In another variation, the high-energy phosphate source is ATP or GTP. As noted previously, any of these reagents may be labeled.

In a further embodiment of the disclosed assay systems, the enzyme comprises a kinase enzyme or a catalytically active polypeptide portion thereof. In one variation, the kinase is histidine protein kinase. In a further variation, the substrate comprises a bacterial or microbial protein or polypeptide molecule. For example, the substrate may comprise a SpoOF protein or a polypeptide portion thereof. In other embodiments, the substrate further includes a linker. In one variation, the linker comprises one or more amino acid residues attached to the substrate. In various preferred embodiments, the linker is attached to the substrate at its N- or C-terminus. In one preferred variation, the linker comprises one or more histidine residues attached to the substrate at its N-terminus.

In yet another embodiment of the within-disclosed assay systems, the solid support may comprise a resin. In one variation, the resin is a Ni-resin. As those of skill in the art will appreciate, various combinations of the foregoing components and various modifications to the above-noted embodiments may be made without exceeding the scope of the within-disclosed and claimed inventions.

BRIEF DESCRIPTION OF THE DRAWINGS

In FIG. 3A, ATP concentration (in µM) is plotted against cpm, and $k_m$=70 µM; in FIG. 3B, ATP concentration (in µM) is plotted against Phospholmager #, and $k_m$=72 µM. The phosphorylation reaction was carried out at 22° C. for 20 min with 30 µl His-SpoOF resin per reaction and 1 µM KinA. The ratio of [$\gamma$-$^{32}$P]ATP to ATP was 1 µCi: 100 µM for all the data points. The solid lines represent the fitting of the data in a Michaelis-Menten equation with indicated $k_m$ values. Each curve is representative of three independent experiments. FIG. 3A: scintillation counting; FIG. 3B: SDS-PAGE analysis.

DETAILED DESCRIPTION OF THE INVENTION

A. Definitions

Figure 1:
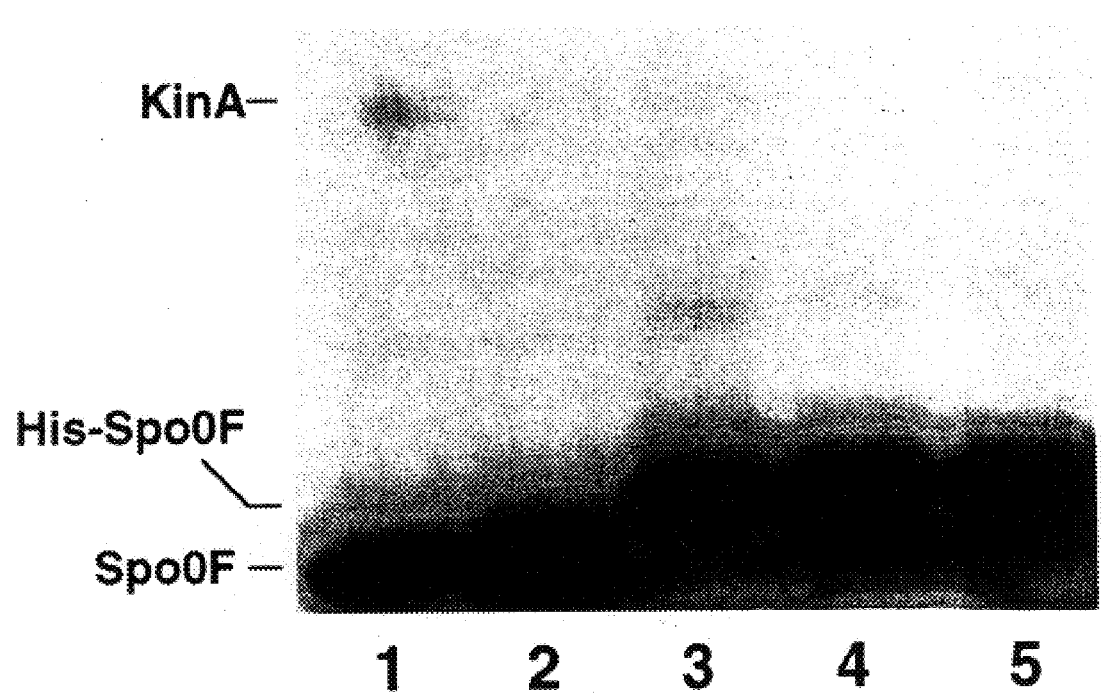
FIG. 1 illustrates the phosphorylation of SpoOF including a histidine linker or tag ("His-SpoOF") by KinA. SpoOF and His-SpoOF were phosphorylated by 1 µM KinA in a volume of 30 µl in the presence of 100 µM ATP and 1 µCi [$\gamma$-$^{32}$P]ATP (>5000 µCi/mmol) at 22° C. for 10 min. The phosphorylation reactions were then analyzed by SDS-PAGE and autoradiography. His-SpoOF was immobilized onto Ni-resin, phosphorylated on a filter plate, and analyzed by SDS-PAGE and autoradiography as described in Example 1 herein. Lanes 1 and 2: 5 µg and 10 µg SpoOF, respectively; lanes 3 and 4: 5 µg and 10 µg His-SpoOF, respectively; lane 5: immobilized His-SpoOF.

Amino Acid Residue: An amino acid, e.g., one formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in J. Biol. Chem. 243: 3552–59 (1969) and adopted at 37 C.F.R. §1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxy-terminus. In addition, the phrase "amino acid residue" is broadly defined to include the amino acids listed in the Table of Correspondence and modified and unusual amino acids, such as those listed in 37 C.F.R. §1.822(b)(4), and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxy-terminal group such as COOH.

The term conservative substitution as used herein is meant to denote that one amino acid residue has been replaced by another, biologically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like. The term "conservative substitution" also includes the use of a substituted amino acid in place of an unsubstituted parent amino acid provided that such a polypeptide also displays the requisite binding activity.

In some instances, the replacement of an ionic residue by an oppositely charged ionic residue such as Asp by Lys has been termed conservative in the art in that those ionic groups are thought to merely provide solubility assistance. In general, however, if the replacements discussed are on relatively short synthetic polypeptide antigens, as compared to a whole protein, replacement of an ionic residue by another ionic residue of opposite charge is considered herein to be a "radical replacement", as are replacements between nonionic and ionic residues, and bulky residues such as Phe, Tyr or Trp and less bulky residues such as Gly, Ile and Val.

The term correspond in its various grammatical forms is used herein and in the claims in relation to polypeptide sequences to mean the polypeptide sequence described plus or minus up to three amino acid residues at either or both of the amino- and carboxy-termini and containing only conservative substitutions in particular amino acid residues along the polypeptide sequence.

Polypeltide and Peptide: Polypeptide and peptide are terms used interchangeably herein to designate a series of no more than about 50 amino acid residues connected one to the other by peptide bonds between the alpha-amino and carboxy groups of adjacent residues.

Protein: Protein is a term used herein to designate a [linear] series of greater than 50 amino acid residues connected one to the other as in a polypeptide.

Receptor: Receptor and receptor protein are terms used herein to indicate a biologically active proteinaceous molecule that specifically binds to (or with) other molecules.

Substantially homologous means that a particular subject sequence or molecule, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 90 percent similarity, equivalent biological activity, and equivalent expression characteristics are considered substantially homologous and are included within the scope of proteins defined by the terms "kinase" and "protein kinase". Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents.

As used herein, the terms pharmaceutically acceptable, physiologically tolerable and its grammatical variations, as they refer to compositions, carriers, diluents and reagents, are used interchangeably and represent that the materials are capable of administration to or upon a mammal without the production of allergic or similar untoward physiological effects such as nausea, dizziness, gastric upset and the like, particularly when administered to a human.

The term physiologically administrable composition as used herein refers to solutions, suspensions and mixtures that are capable of being readily provided into the body of a mammal by parenteral, oral or rectal administration and includes injectable solutions, emulsions and the like.

Various symbols will also be used throughout; unless otherwise defined, such symbols are used in a manner consistent with usage understood in the relevant art. For example, the symbol "~" which often precedes the letter "P" in certain descriptions/equations, represents a high-energy bond.

The term unit dose when used in reference to a therapeutic composition of the present invention refers to physically discrete units suitable as unitary dosages for humans, each unit containing a predetermined quantity of active material calculated to produce the desired therapeutic effect in association with the required diluent, i.e., carrier, or vehicle.

The within-described compositions are administered in a manner compatible with the dosage formulation, and in a therapeutically effective amount. The quantity to be administered depends on the subject to be treated, and capacity of the subject to utilize the active ingredient. Precise amounts of active ingredient required to be administered depend on the judgment of the practitioner and are peculiar to each individual. However, suitable dosage ranges are of the order of one to several milligrams of active ingredient per individual per day and depend on the route of administration.

Suitable regimens for initial administration and booster shots are also variable, but are typified by an initial administration followed by repeated doses at one or more hour intervals, by a subsequent injection or other administration. Alternatively, continuous intravenous infusion sufficient to maintain therapeutically effective concentrations in the blood are contemplated.

B. The Two-Component Regulatory Switch

1. General Backaround

Recently, it has become apparent that bacteria respond to environmental stress by activating the transcription of genes which modify the bacterial cells/organisms for adaptation to the new environment. Environmental stressors such as osmotic shock, alterations in electrolyte balance, nitrogen starvation, phosphate or carbon-source deprivation, or changes in oxygen concentration may induce specific metabolic pathways and/or biochemical systems which allow the bacterial organism to retain or develop the capacity to cope with the new environmental status. Other, more common bacterial processes may also trigger these adaptive systems or pathways; such processes include or involve motility, chemotaxis, secretion of enzymes, transport of hexoses, and the capacity for virulence. All of these systems share a common "trigger"; i.e., a signal induces a transcriptional change via what is described herein as a two-component regulatory switch.

These two-component regulatory switches generally comprise a histidine protein kinase that may be activated to autophosphorylate by the signal transduction mechanism. Once this has occurred, the phosphorylated kinase then acts as a phosphotransferase to phosphorylate a particular region, usually the amino-terminal domain, of a regulatory protein that ultimately influences the transcription of one or more nucleotide sequences or genes.

The core of the signal transduction system for the initiation of sporulation is a series of phosphotransfer reactions that we have termed a phosphorelay. The phosphorelay is a significant variant of the two-component stimulus-response mechanism used to control environmental responses in bacteria (see, e.g., Stock et al., *Nature* 344: 395–400 (1990). In their simpler forms such systems use a signal-transducing transmitter protein kinase to phosphorylate a response regulator; the latter protein in many systems is a transcriptional activator. In the phosphorelay, on the other hand, the phosphate group from one response regulator is transferred to a second response regulator by the SpoOB protein phosphotransferase. The SpoOB protein phosphotransferase has no known homology to transmitter kinases, suggesting that the homology observed in such kinases may be related to the binding of ATP and the autophosphorylation reaction (see, e.g., Stock, et al., Id.).

Several things have become apparent from our study of such two-component regulatory switches in a variety of bacterial genera and species. First, the histidine protein kinases all share regions of homology, which suggests that they originated from a common progenitor gene. Second, the amino-terminal domain of the phosphoreceptor protein is highly conserved from genus to genus within the bacteria and from one regulatory system to the next. Finally, this type of two-component regulatory switch seems to be unique to bacteria.

Therefore, the two-component regulatory switches appear to comprise a unique target for antimicrobial therapy in higher organisms, including man, without the likelihood of encountering the two-component system in the organism receiving treatment. It is proposed herein that the design of antimicrobial antibiotics may be accomplished by rational drug design methodology following elucidation of the structure of the kinase and its conserved regulatory target domain.

2. A Two-Component Switch in Bacillus

Sporulation in *Bacillus subtilis* is controlled by a phosphorelay mechanism (Burbulys, et al., *Cell* 64: 545–552 (1991)). One of the first steps in the process involves the activation of the protein kinase encoded by the KinA gene. The KinA enzyme is a member of a unique class of bacterial protein kinases that are needed for adaptation and survival in adverse environments (Bourret, et al., *Ann. Rev. Biochem.* 60: 401–441 (1991)). Because of the essential nature of these kinases and their seemingly ubiquitous occurrence in bacterial cells, identification of factors inhibiting the activity of these kinases could lead to the development of a new class of antibiotics.

These kinases show a very high degree of sequence homology in their carboxyl-terminal halves, therefore, an inhibitor that functions through an interaction with this portion of one member of the class is very likely to be an inhibitor of other members of the class. We have been investigating factors that affect the activity of the KinA enzyme not only to better understand its specific role in sporulation but also to identify and possibly exploit inhibitory compounds that may function as broad-spectrum antibiotics.

Our initial observations, which supported our belief that two-component switches represent a promising target of new antibiotics, indicated that certain fatty acids inhibit the activity of the KinA enzyme in vitro. Our data, including that reported herein, suggests that the strongest fatty acid-derived inhibitors have a chain length of about 16–20 carbon atoms with at least one cis-unsaturated bond within 11 carbon atoms of the carboxyl group. Isomers having a double bond in the trans configuration are not inhibitory. Additional evidence suggests that other fatty acids meeting the above criteria, but which include methyl groups branching from the main chain, may be even more inhibitory. While these particular fatty acids themselves may not be useful as antibiotics, per se, analysis of their chemical and structural features is providing new insights, leading to the design and synthesis of new antibiotics.

The initiation of sporulation in *B. subtilis* is controlled by the SpoOA transcription factor which is activated by phosphorylation through a phosphorelay mechanism dependent upon the activity of one or more protein kinases. The enzymatic activity of one of these protein kinases, KinA, was found to be inhibited in vitro by certain fatty acids, as noted above. Saturated straight- or branched-chained fatty acids are either much weaker inhibitors or have no effect when compared to the fatty acid inhibitors with an unsaturated double-bond in the cis configuration. The inhibitors prevent autophosphorylation of KinA and are non-competitive with ATP.

*B. subtilis* phospholipids were found to contain at least one as yet unidentified type of fatty acid that, when present in an unesterified form, inhibited KinA. The results suggests that the concentration of a specific unsaturated fatty acid may act as a signal linking the initiation of sporulation to the status of membrane synthesis and septation or some other specific membrane-associated activity.

To elucidate how and why a cell undergoes a developmental transition, two fundamental questions must be addressed. First, what are the metabolic and environmental signals that initiate the process; and second, how are these signals then relayed to the cellular machinery in order to bring about alterations in gene expression. Sporulation of *B. subtilis* cells in response to nutrient deprivation is a useful system for studying simple cellular differentiation at the molecular level.

The basic features of a signal transduction mechanism involved in the primary stages of this process have been described (Burbulys, et al., *Cell* 64: 545–552 (1991); Trach, et al., *Res. Microbiol.* 142: 815–823 (1991)). However, the exact nature of the metabolic and environmental signals responsible for activating the system are largely unknown. The first tangible effects of these signals is to trigger the autophosphorylation of one or more protein kinases—predominately that encoded by the KinA gene (Burbulys, et al., *Cell* 64: 545–552 (1991); Antoniewsky, et al., *J. Bacteriol.* 172: 86–93 (1990); Perego, et al., *J. Bacteriol.* 171: 6187–6196 (1989)). The signals, now in the form of phosphate groups, are then transferred to the SpoOF protein. Because it can be phosphorylated by different sensor kinases, SpoOF plays the role of a secondary messenger which integrates the various input signals and channels the information into the subsequent steps of this pathway; this pathway has been termed a phosphorelay (Burbulys, et al., Id. (1991)). The phosphate group on SpoOF~P is transferred to the SpoOA protein in a reaction catalyzed by the phosphoprotein-phosphotransferase encoded by the SpoOB gene.

Phosphorylated SpoOA is a transcription regulator that serves to "reprogram" gene expression during the initial stages of sporulation. It functions as both a repressor and an activator of transcription. Among other activities, it represses transcription of the abr, gene (Strauch, et al., *PNAS USA* 87: 1801–1805 (1990)), leading to the expression of genes that are under AbrB control (Strauch and Hoch, in *Bioloay of Bacilli; Applications to Industry*, Doi (ed.), Butterworth-Heine-Mann, Stoneham, Mass., pp. 105–121 (1992); Strauch, in *Bacillus subtilis and Other Gram Positive Bacteria*, Losick, et al., eds.(1992); Strauch, et al., *EMBO J.* 8: 1615–1621 (1989)), and it activates expression of the spoIIA and spoIIG operons which contain genes encoding sporulation-specific RNA polymerase sigma factors (Trach, et al., *Res. Microbiol.* 142: 815–823 (1991); Satola, et al., *PNAS USA* 88: 4533–4537 (1991)).

The signals that lead to autophosphorylation of the sensor kinases are largely unknown. In order to unearth the answers, we have expressed and purified the KinA enzyme (Perego, et al., *J. Bacteriol.* 171: 6187–6196 (1989)) and an extensive search for affecters of its activity in vitro has been conducted (unpublished data). It is reported herein that cis-unsaturated fatty acids such as oleic, cis-vaccenic, and palmitoleic acids are potent inhibitors of the autophosphorylation of KinA. Methods of identifying other useful inhibitors are also described herein.

In contrast, trans isomers, including elaidic and trans-vaccenic fatty acids, saturated forms such as stearic and palmitic fatty acids, and iso-branched species, have little or no inhibitory effect. A total phospholipid extract of *B. subtilis* also had no inhibitory effect. However, when these phospholipids were treated to release free fatty acids, the extracted fatty acid mixture was inhibitory, implying the presence of naturally-occurring fatty acids that regulate KinA.

It should also be understood that various combinations of the embodiments described herein are included within the scope of the present invention. Other features and advantages of the present invention will be apparent from the descriptions hereinabove, from the Examples to follow, and from the claims.

C. Assay Systems and Methods

One useful assay method disclosed herein comprises admixing a "test" sample—e.g., a composition or compound that one wishes to evaluate for potential antibacterial, antimicrobial or antibiotic applications—with the within-described substrate or sensor protein. The reaction admixture thus formed is preferably maintained under appropriate assay conditions—e.g., for a time period sufficient for the substrate to become phosphorylated (or not), depending upon the inhibitory effect of the test sample.

Any reaction product is then preferably separated from any unreacted antibodies present in the admixture. The presence—and if desired, the amount—of reaction product formed is then determined. The amount of product formed may then be correlated with the amount of receptors expressed by the cells, or with the amount of soluble antigen expressed.

Determination of the presence or amount of immunoreaction product formed depends upon the method selected for identifying the product. For instance, a labeled antibody may be used to form a labeled immunocomplex with a protein or polypeptide molecule of the present invention (e.g., a substrate or a sensor protein). The labeled immunocomplex may be quantitated by methods appropriate for detecting the respective label—e.g., fluorescent labels, radioactive labels, biotin labels and the like—as discussed herein.

In a further aspect of the invention, data obtained in the instant assays are recorded via a tangible medium, e.g., computer storage or hard copy versions. The data can be automatically input and stored by standard analog/digital (A/D) instrumentation that is commercially available. Also, the data can be recalled and reported or displayed as desired for best presenting the instant correlations of data. Accordingly, instrumentation and software suitable for use with the present methods are contemplated as within the scope of the present invention.

With particular regard to assay systems packaged in "kit" form, it is preferred that assay components be packaged in separate containers, with each container including a sufficient quantity of reagent for at least one assay to be conducted. As further described herein, one or more reagents may be labeled; alternatively, a labeling agent may be provided in the kit in its own container.

A preferred kit is typically provided as an enclosure (package) comprising one or more containers for the within-described reagents. Typically, the kit also contains a labeling agent to signal the formation of a reaction product.

The label may be any of those commonly available, including, without limitation, fluorescein, phycoerythrin, rhodamine, $^{125}I$, and the like. Other exemplary labels include $^{111}In$, $^{99m}Tc$, $^{67}Ga$, $^{132}I$, $^{32}P$, and nonradioactive labels such as biotin and enzyme-linked antibodies. Any label or indicating means that may be linked to or incorporated in a protein or polypeptide molecule is contemplated by the present invention. A contemplated label may also be used separately, and those atoms or molecules may be used alone or in conjunction with additional reagents. Many useful labels of this nature are known in clinical diagnostic chemistry.

The linking of labels to polypeptides and proteins is also well known. For instance, antibody molecules produced by a hybridoma may be labeled by metabolic incorporation of radioisotope-containing amino acids provided as a component in the culture medium. See, for example, Galfre et al., *Meth. Enzvmol.* 73: 3–46 (1981). The techniques of protein conjugation or coupling through activated functional groups are particularly applicable. See, for example, Aurameas, et al., *Scand. J. Immunol.*, Vol. 8, Suppl. 7: 7–23 (1978), Rodwell et al., *Biotech.*, 3: 889–894 (1984), and U.S. Pat. No. 4,493,795 (the latter of which is incorporated by reference herein).

An instant diagnostic system may also include a specific binding agent. A "specific binding agent" is a chemical species capable of selectively binding a reagent species of the present invention but is not itself a reagent species of the present invention. Exemplary specific binding agents include antibody molecules, complement proteins or fragments thereof, protein A and the like. Such specific binding agents may be useful as labeling agents. In various embodiments, the specific binding agent is labeled. However, when the system includes a specific binding agent that is not labeled, the agent is typically used as an amplifying means or reagent. In these embodiments, a labeled specific binding agent is capable of specifically binding the amplifying means when the amplifying means is bound to a complex containing one of the instant reagents.

In preferred embodiments, one of the reagent components may be affixed to a solid matrix to form a solid support that is separately packaged in the subject assay systems or kits. The reagent may be affixed to the solid matrix by adsorption from an aqueous medium, although other modes of affixation well known to those skilled in the art may be used, such as specific binding methods. Other means of linking a reagent molecule to a solid support are disclosed herein. For example, histidine residues located at the N-terminal end of a substrate molecule as described herein may effectively be used to link such a molecule to a solid support.

Useful solid matrix materials include the derivatized cross-linked dextran available under the trademark SEPHADEX from Pharmacia Fine Chemicals (Piscataway, N.J.), agarose in its derivatized and/or cross-linked form, polystyrene beads about 1 micron to about 5 millimeters in diameter (available from Abbott Laboratories of North Chicago, Ill.), polyvinyl chloride, polystyrene, cross-linked polyacrylamide, nitrocellulose- or nylon-based webs such as sheets, strips, tubes, plates, the wells of a microtiter plate such as those made from same or from polystyrene, polyvinylchloride, and the like. A preferred solid matrix (support) comprises Ni-resin (nickel-conjugated exchange resin).

The reagent species, labels, or labeled specific binding agents described herein may be provided in solution, as a liquid dispersion or as a substantially dry powder, e.g., in lyophilized form. Where the reagent is an enzyme, the enzyme's substrate may also be provided in a separate package of a kit or system. Usually, the reagents are packaged under an inert atmosphere. A solid support such as the before-described microtiter plate and one or more buffers may also be included as separately packaged elements in this diagnostic assay system.

The diagnostic system is usually contained in a conventional package. Such packages include glass and plastic (e.g., polyethylene, polypropylene and polycarbonate) bottles, vials, plastic and plastic-foil laminated envelopes and the like.

Printed instructions providing guidance in the use of the packaged reagent(s) may also be included, in various preferred embodiments. The term "instructions" or "instructions for use" typically includes a tangible expression describing the reagent concentration or at least one assay method parameter, such as the relative amounts of reagent and sample to be admixed, maintenance time periods for reagent/sample admixtures, temperature, buffer conditions, and the like.

While histidine protein kinase is discussed hereinbelow as a preferred sensor protein, it is expressly to be understood that other proteins (and polypeptide portions thereof) derived from a wide variety of bacterial species (including, but not limited to, B. subtilis) are contemplated by the present invention. Thus, for example, a useful sensor protein according to the present invention may comprise a polypeptide exhibiting homology in sequence to a polypeptide portion of a protein kinase. In addition, a protein or polypeptide according to the present invention may correspond to a sequential subset of an active sensor protein, wherein "sequential subset" refers to the fact that a polypeptide has an amino acid residue sequence corresponding to that of a subset of the amino acid residue sequence of a larger protein or polypeptide. For example, if "ABCDEFGH" were a polypeptide, exemplary sequential subsets thereof would include "ABC", "BCDE", "DEFGH", "ABCDEFG", and so forth; conversely, "ACDB" would not be included in such a subset.

EXAMPLES

The following examples illustrate, but do not limit, the present invention.

Example 1

High Throughput Assay

The within-disclosed high throughput assay for histidine protein kinase is particularly useful for inhibitor screening purposes. An assay system for histidine protein kinase activity without SDS-PAGE separation or acid precipitation is further described. *Bacillus subtilis* KinA (histidine protein kinase) and SpoOF (cognate response regulator) are used as kinase and substrate, respectively. This assay system can also be applied to other protein kinases and their substrates. The kinetic features of the system, and the adaptation of the within-disclosed assay system into a high throughput assay for histidine protein kinases, are also presented herein.

A. Materials & Methods

*Bacillus subtilis* KinA and SpoOF were expressed in *E. coli* and purified according to known methods (see, e.g., Perego, et al., *J. Bacteriol.* 171: 6187–96 (1989); Trach and Hoch, *Molec. Microbiol.* 8: 69–79 (1993)), and as set forth hereinbelow.

1. KinA Purification Protocol a. Cell Growth

Select one small colony of *B. subtilis* from a fresh plate—preferably one stored at 4° C. and not older than four weeks. Inoculate 2 ml×2 of Luria broth (LB) supplemented with 100 µg/ml ampicillin. Allow the culture to grow at 37° C., with shaking (300 rpm) for 7–8 hr. Inoculate 250 ml LB supplemented with 100 µg/ml ampicillin with the 2.0 ml culture and allow to grow at 37° C., with shaking (300 rpm) overnight.

The following morning, take 25 ml of culture and inoculate 1 liter of LB +100 µml ampicillin. Allow to grow at 37° C., with shaking (200 rpm) until O.D.$_{600}$=0.5–0.7 (about 3.5 hr). Transfer flasks to 30° C. and grow for one hour. Induce with 0.2 mM IPTG and grow 3–4 hr at 30° C., with shaking (300 rpm).

Harvest the cells, wash with sonication buffer (put all cells in one tube) and store at −70° C.

b. Purification

All the following steps should preferably be carried out at 4° C. To every gram of cells, add 5 ml sonication buffer with protease inhibitors and re-suspend the cells to even cell suspension. Sonication may be formulated as follows: 25 mM Tris, ph 8.0 (at 4° C.); 1 mM EDTA; 1 mM BME; and 10 mM KCl. Protease inhibitors may be formulated as follows:

|  | Stock | Final concentration |
|---|---|---|
| PMSF | 100 mM in EtOH | 1 mM |
| Pepstatin | 2 mg/ml in MeOH | 2 µg/ml |
| Leupeptin | 2 mg/ml | 2 µg/ml |

Preferably, protease inhibitor should not be added to the sonication buffer until one is about to use it.

Sonicate the cell suspension (on ice) using the large tip. Preferably, use 30–40 second bursts each time, for 5 times. Then, spin the cell suspension for 30 minutes at 18,000 rpm.

Measure the volume of the supernatant. Add the required amount of saturated NH$_4$SO$_4$ solution for 35% saturation. Add slowly to solution that is slowly stirring on a stir plate in an ice bath. After all the NH$_4$SO$_4$ is added, stir for an additional 30 min. Spin for 30 min. At 18,000×g. The KinA should be in the pellet; the supernatant may be saved for use in gels.

Re-suspend pellets in 70 ml (for cells from 10 liter culture) sonication buffer and inhibitors. Carry this step out carefully and gently; do not vortex. Attempt to dissolve the pellet as completely as possible.

Dialyze the sample against 4 liters of sonication buffer for 1 hour. Change to another 4 liters of sonication buffer and dialyze for another hour. Spin at 18,000 rpm (18,000×g) for 20 min. before loading.

Set up a 40 ml Affigel column (for cells from 10 liter culture) equilibrated in sonication buffer. Load sample on the column at about 1 ml/min, followed by an extensive wash (until Abs$_{280}$=0.001). Elute with sonication buffer with 1 M KCl.

Pool fractions with Abs$_{280}$>0.1. Dialyze the pooled samples against 4 liters of sonication buffer immediately, with a change of buffer every hour for a total of 3×4 liters. The fractions may be left overnight in the third 4 liter buffer, if necessary.

Set up a 20 ml Q-Sepharose column on FPLC (for cells from 10 liter culture). Start by washing both pumps; wash with 40 ml 1 M NaCl at 2 ml/min followed by 100 ml S.B. at 3 min/ml. Wash pump C and superloop.

Load sample at 2 ml/min, followed by a wash in sonication buffer. When Abs$_{280}$ nears 0.001, wash column with sonication buffer with about 300 ml 200 mM KinA. A fairly good peak should elute here which contains no KinA. Elute KinA with a 200 mM–300 mM KCl gradient in sonication buffer for a total volume of 250 ml. Measure the Abs$_{280}$ of the fractions in the peak(s). AT this juncture, one can estimate the KinA concentration by using Abs$_{280}$, 1 mg/ml=1.

Measure ATPase activity of the above fractions based on equal amounts of protein. Pool the fractions containing low ATPase activity for HTP assay. Dialyze the pool in 4 liters of storage buffer for 1 hour, with one change for another hour.

Dialyze in 4 liter storage buffer with 40% glycerol overnight. Storage buffer: 50 mM Tris-HCl, pH 8.0 at 4° C., plus 1 mM B-ME.

Aliquot KinA in small aliquots and store at −20° C.

2. SpoOF Purification

SpoOF may be purified according to standard protocols. (See, e.g., Burbulys, et al., *Cell* 64: 545–552 (1991).) Purification of His-SpoOF is carried out as described hereinbelow.

SpoOF including a histidine linker sequence (also identified herein as "His-tagged SpoOF" or "His-SpoOF") was constructed, expressed, and purified using the pET16 expression system from Qiagen (Chatsworth, Iowa) by following the manufacturer's instructions. The recombinant proteins were determined to be of 95% or greater purity via SDS-PAGE analysis. The concentration of SpoOF was determined using the extinction coefficient ($\epsilon_{275}$ nm=7000 $M^{-1}cm^{-1}$) (Kentebe, et al., unpublished results). The concentration of His-SpoOF was determined using the BCA kit from Pierce Chemicals (Rockford, Ill.) using SpoOF as the standard. The concentration of KinA was determined using the Bradford assay with bovine serum albumin as the standard. All chemicals used were obtained from Sigma (St. Louis, Mo.) except [$\gamma$-$^{32}$P]ATP (>5000 Ci/mmol), which was obtained from Amersham (Arlington Heights, Ill.).

B. Phosphorylation Assay

KinA-mediated phosphorylation of SpoOF was carried out in 50 mM EPPS buffer (pH 8.5) containing 20 mM $MgCl_2$, 0.1 mM EDTA, and 5% glycerol in a total volume of 30 $\mu$l. KinA, SpoOF or His-SpoOF, ATP and [$\gamma$-$^{32}$P]ATP were included at indicated concentrations. After incubation at 22° C. for the designated period of time, the reaction was terminated by addition of 7.5 $\mu$l of 5× SDS-PAGE loading dye containing 272 mM Tris-HCl, pH 6.8, 1.4% SDS, 22% glycerol, and 313 mM 2-mercaptoethanol. The samples were immediately frozen on dry ice until just prior to SDS-PAGE analysis.

Samples were loaded onto a 10% to 20% gradient gel and electrophoresed according to the method of Laemmli, (*Nature (London)* 227: 680–685 (1970)) until the dye front had migrated for about 80% of the gel length. The lower portion of the gel containing the dye front was removed to reduce background radiation due to unincorporated [$\gamma$-$^{32}$P] ATP. The gel was briefly washed with water. After removal of excess water, the gel was covered with plastic wrap and exposed for 1 to 3 hours to a PhosphoImager screen from Molecular Dynamics (Sunnyvale, Calif.). Quantitation of the radioactivity of each band was done with the PhosphoImager system. In some cases, known amounts of radioactivity were spotted onto a piece of filter paper and exposed to the screen with the gel and used as standards to convert the reading form PhosphoImager to cpm for the samples.

C. Binding of His-SpoOF to Ni-Resin

Purified His-SpoOF, at 1 mg/ml in 50 mM Tris-HCl, pH 8.0, 100 mM KCl, 20 mM $MgCl_2$, 0.1 mM EDTA, and 5% glycerol (buffer A), was mixed with 0.4 volume of 50% (v/v) Ni-resin in buffer A. The mixture was incubated at 4° C. with shaking for three hours. After a brief spinning, the supernatant was separated from the resin and subjected to BCA assay to determine the amount of unbound His-SpoOF. The resin was washed with buffer A three times and resuspended in buffer A to a final concentration of 25% (v/v). The binding efficiency of His-SpoOF to the Ni-resin was 92%±4.2% (n=5). The specificity of the resulting resin was approximately 1 $\mu$g of His-SpoOF/$\mu$l.

D. Phosphorylation of His-SpoOF Bound to the Ni-Resin

Phosphorylation of immobilized His-SpoOF was carried out using the MultiScreen 96-well filtration plate (0.65 $\mu$m, type DVPP) from Millipore (Bedford, Mass.). The removal of liquid from the wells of the filtration plate was done with the vacuum manifold from Millipore. The His-SpoOF resin (25%, v/v) was placed into individual wells of the filtration plate and washed twice with 200 $\mu$l buffer A. A total volume of 80 $\mu$l of buffer A containing the indicated amounts of KinA, ATP, and [$\gamma$-$^{32}$P]ATP was added to the wells.

At this juncture, concurrent with or prior to the addition of ATP, a predetermined amount and concentration of a test sample—i.e., a compound or composition being evaluated for its inhibitory effect on the relevant sensor protein or enzyme—is also added to the wells. Preferably, one or more wells are run as "controls"—i.e., with no test sample(s) added. While much of the following description primarily discusses the running of the high throughput assays without reference to the evaluation of a test sample, it is expressly to be understood that use of the within-disclosed system and methods to identify new and useful antibiotic, antimicrobial, and antibacterial agents is clearly contemplated.

The plate was then incubated for the indicated period of time at 22° C. with gentle shaking. The reaction was terminated by removal of the reaction mixture from the wells followed by three washes of the resin with buffer A.

The resin was then washed three times with buffer A containing 30 mM imidazole with 5 min. incubation/shaking and another three times with buffer A only. For analysis by SDS-PAGE, 80 $\mu$l of 1.5× SDS-PAGE loading dye containing 0.5 M imidazole was added to each of the wells and the plate was incubated at 22° C. with shaking for 5 minutes. The content of each well except the resin was then collected into another 96-well plate by using the vacuum manifold and 40 $\mu$l from each well was loaded onto a 10% to 20% gradient gel. The gel was electrophoresed and processed as described above.

For analysis by scintillation counting, 80 $\mu$l of 0.2 N HCl was added to each of the wells and the plate was incubated at 55° C. with gentle shaking for 1 hour. The content of each well except the resin was collected into a 96-well MicroFluor plate (Dynatech, Chantilly, Va.) by using the vacuum manifold. To each of the wells of the MicroFluor plate, 150 $\mu$l of MicroScint-40 (Packard, Meriden, Conn.) was added and the radioactivity was counted using the TopCount from Packard.

E. Results

SpoOF with six extra histidine residues at the N-terminus (His-SpoOF) was phosphorylated by KinA in the presence of ATP to the same extent as the wild-type SpoOF using the conventional phosphorylation assay (see part A hereinabove—"Materials and Methods"—and FIG. 1).

It should also be noted that while SpoOF with a linker comprised of six histidine residues is described herein as preferred, it is to be expressly understood that one may alter the number of His residues used —i.e., using 1 or more His residues—or one may use other amino acids as linkers, and still fall within the scope of the disclosed invention. In addition, other linker molecules are available for use to attach substrates to a solid support; such molecules are also contemplated for use as described herein.

FIG. 1 illustrates the phosphorylation of His-SpoOF by KinA. SpoOF and His-SpoOF were phosphorylated by 1 $\mu$M KinA in a volume of 30 $\mu$l in the presence of 100 $\mu$M ATP and 1 $\mu$Ci [$\gamma$-$^{32}$P]ATP (>5000 $\mu$Ci/mmol) at 22° C. for 10 min. The phosphorylation reactions were then analyzed by SDS-PAGE and autoradiography. His-SpoOF was immobilized onto Ni-resin, phosphorylated on a filter plate, and analyzed by SDS-PAGE and autoradiography as described hereinabove. Lanes 1 and 2: 5 $\mu$g and 10 $\mu$g SpoOF, respectively; lanes 3 and 4: 5 $\mu$g and 10 $\mu$g His-SpoOF, respectively; lane 5: immobilized His-SpoOF.

When immobilized onto the Ni-resin, His-SpoOF was also phosphorylated by KinA as shown in FIG. 1 (lane 5).

These results demonstrated that the addition of extra histidine residues at the N-terminus of SpoOF, as well as attaching His-SpoOF to Ni-resin via these histidine residues, did not prevent SpoOF from being a substrate for KinA-mediated phosphorylation.

In the conventional phosphorylation assay, the KinA and SpoOF were separated from [γ-$^{32}$P]ATP by SDS-PAGE and measured by autoradiography. With His-SpoOF being immobilized onto the Ni-resin, the separation of His-SpoOF from KinA and [γ-$^{32}$P]ATP was achieved by simple removal of the reaction mixture from the resin (see section A hereinabove). Subsequently, it should be possible to measure the phosphorylation of His-SpoOF by determining the amount of radioactivity remaining on the resin.

To confirm this possibility, phosphorylation of immobilized His-SpoOF by KinA and separation of the His-SpoOF from the rest of the reaction components were carried out as described in section A hereinabove. The resulting His-SpoOF resin was subject to both scintillation counting after acid hydrolysis of the His-SpoOF phosphate, and SDS-PAGE after elution of the His-SpoOF from the resin with SDS-PAGE loading buffer containing 0.5<imidazole.

The results of the foregoing are summarized in Table 1. As shown in Table 1, the amounts of radioactivity from the samples incubated with KinA were much greater than the amounts determined in samples not incubated with KinA, with the latter representing the background radioactivity on the resin.

TABLE 1

Phosphorylation of his-SpoOF Immobilized Onto Ni-Resin

EXPERIMENT 1

| μl of Resin (pmol) | +KinA (cpm) | −KinA (cpm) | SpoOF~P |
|---|---|---|---|
| 5 | 2715 ± 242 | 219 ± 40 | 19 |
| 10 | 4264 ± 248 | 167 ± 28 | 31 |
| 20 | 4989 ± 125 | 177 ± 82 | 36 |
| 30 | 4953 ± 88 | 250 ± 61 | 36 |
| 40 | 4876 ± 205 | 222 ± 35 | 35 |
| 50 | 4381 ± 75 | 260 ± 43 | 31 |

EXPERIMENT 2

| μl of Resin | +KinA (cpm) | −KinA (cpm) | SpoOF~P (pmol) | SDS-PAGE PI* # |
|---|---|---|---|---|
| 5 | 4189 ± 103 | 363 ± 76 | 20 | 33758 |
| 10 | 5624 ± 136 | 241 ± 48 | 27 | 53922 |
| 20 | 7281 ± 361 | 278 ± 80 | 35 | 57648 |
| 30 | 6766 ± 440 | 430 ± 95 | 32 | 52968 |
| 40 | 6277 ± 413 | 245 ± 34 | 30 | 46886 |
| 50 | 6500 ± 325 | 232 ± 37 | 31 | 45862 |

*PI = Phospholmager

The amount of [γ$^{32}$P]ATP was 1 μCi per reaction in Experiment 1, and 2 μCi per reaction in Experiment 2 and SDS-PAGE. Data are presented as mean±S.D. or mean (n=3). The Phospholmager number was the reading from the Phospholmager, which was proportional to the radioactivity in each of the His-SpoOF bands.

Among the samples incubated with KinA, the amount of radioactivity increased as the amount of His-SpoOF resin increased from 5 μl to 20 μl and decreased slightly as the amount of the resin further increased from 30 μμl to 50 μl. Although the cpms of the samples increased when the amount of [γ-$^{32}$P]ATP in the reaction was increased, the amount of SpoOF phosphate, calculated based on the cpm, the isotope dilution factor, and the specificity of the [γ-$^{32}$P]

ATP, was about the same for a given amount of His-SpoOF resin (comparing Experiment 1 and Experiment 2 in Table 1).

These results suggest that the amount of radioactivity remaining on the resin reflected the extent of phosphorylation of the immobilized His-SpoOF. This correlation between the cpm and His-SpoOF phosphorylation was confirmed by the result of SDS-PAGE analysis of the His-SpoOF resin. Phosphorylation of His-SpoOF was determined by measuring the relative radioactivity (presented as the Phospholmager number) in each of the His-SpoOF bands on the gel (results not shown).

The results (see Table 1) not only demonstrated the formation of His-SpoOF-$^{32}$P, they also revealed a pattern of dose-response between the extent of His-SpoOF phosphorylation and the amount of His-SpoOF resin, which was the same as that measured by cpm. This pattern of dose-response to SpoOF was also observed in the conventional phosphorylation assay (data not shown).

Figure 2:
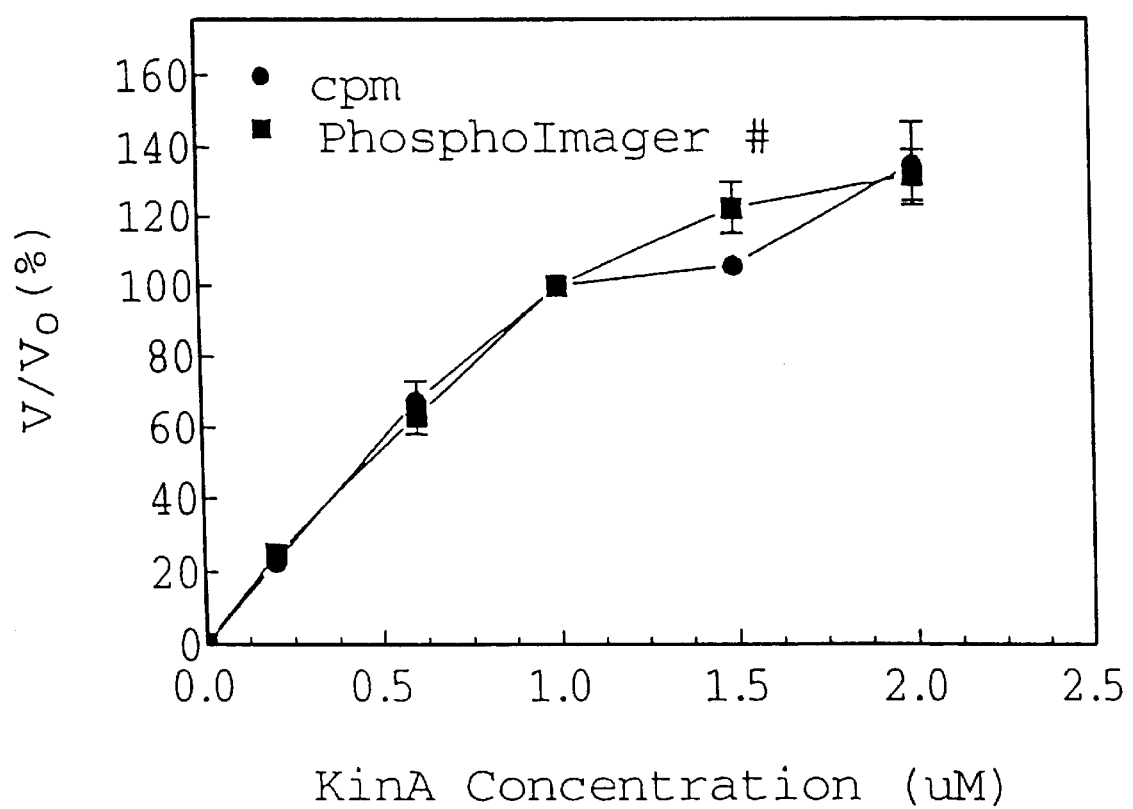
FIG. 2 illustrates the effect of KinA concentration on phosphorylation of immobilized His-SpoOF, with KinA concentration (in µM) plotted against $v/v_0$ (%). Closed squares represent the Phospholmager #, while closed circles represent cpm. The phosphorylation reaction was carried out at 22° C. for 30 min with 30 µl His-SpoOF resin (25%, v/v) and 100 µM ATP containing 1 µCi [$\gamma$-$^{32}$P]ATP per reaction. The data were presented as relative activity to that at 1 µM KinA. Each data point represents the mean of duplicate experiments.

To characterize the kinetic features and to further confirm the correlation between the cpm and phosphorylation of immobilized His-SpoOF in our assay system, the dependence of phosphorylation of His-SpoOF on quantities of KinA and ATP and the time course of the reaction were determined by both scintillation counting and SDS-PAGE analysis. FIG. 2 shows the relationship between extent of His-SpoOF phosphorylation and quantity of KinA.

FIG. 2 illustrates the effect of KinA concentration on phosphorylation of immobilized His-SpoOF, with KinA concentration (in μM) plotted against $v/v_0$. (%). Closed squares represent the Phospholmager #, while closed circles represent cpm. The phosphorylation reaction was carried out at 22° C. for 30 min with 30 μl His-SpoOF resin (25%, v/v) and 100 μM ATP containing 1 μCi [γ-$^{32}$P]ATP per reaction. The data were presented as relative activity to that at 1 μM KinA. Each data point represents the mean of duplicate experiments.

The response was linear up to 1 μM of KinA and approached saturation at KinA concentrations above 1.5 μM. The dependence of phosphorylation of immobilized His-SpoOF on ATP displayed typical Michaelis-Menten saturation as shown in FIG. 3.

Figure 3A:
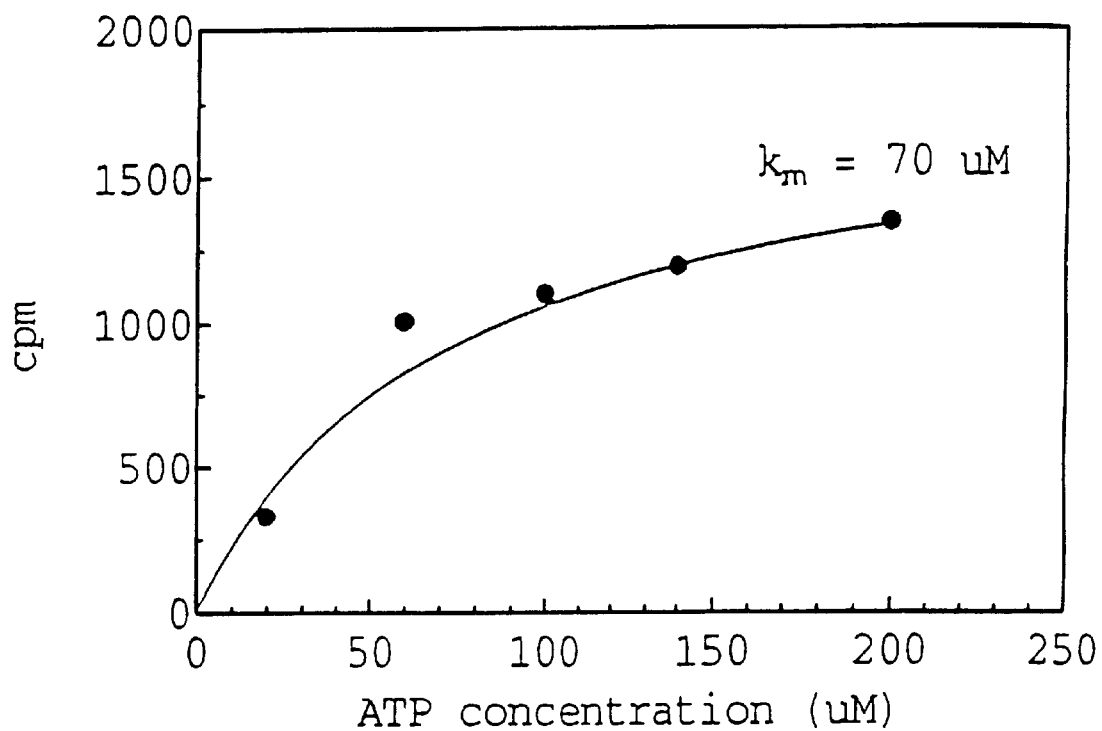
FIGS. 3A and 3B illustrate the phosphorylation of immobilized His-SpoOF at various ATP concentrations.
Figure 3B:
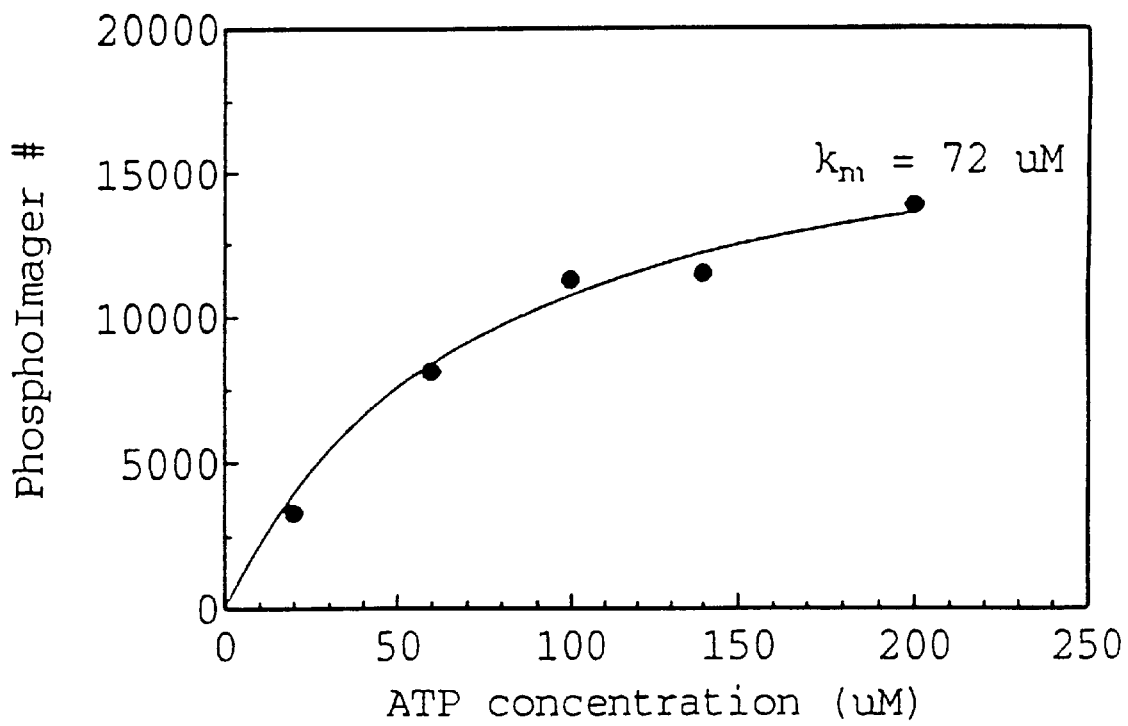

FIGS. 3A and 3B illustrate the phosphorylation of immobilized His-SpoOF at various ATP concentrations. In FIG. 3A, ATP concentration (in μM) is plotted against cpm, and $k_m$=70 μM; in FIG. 3B, ATP concentration (in μM) is plotted against Phospholmager #, and $k_m$=72 μM. The phosphorylation reaction was carried out at 22° C. for 20 min with 30 μl His-SpoOF resin per reaction and 1 μM KinA. The ratio of [γ-$^{32}$P]ATP to ATP was 1 μCi:100 μM for all the data points. The solid lines represent the fitting of the data in a Michaelis-Menten equation with indicated $k_m$ values. Each curve is representative of three independent experiments. FIG. 3A: scintillation counting; FIG. 3B: SDS-PAGE analysis.

From these data the apparent Km value for ATP was estimated to be 70 μM from scintillation counting and 72 μM from SDS-PAGE analysis. The time course of phosphorylation of immobilized His-SpoOF is shown in FIG. 4.

Figure 4:
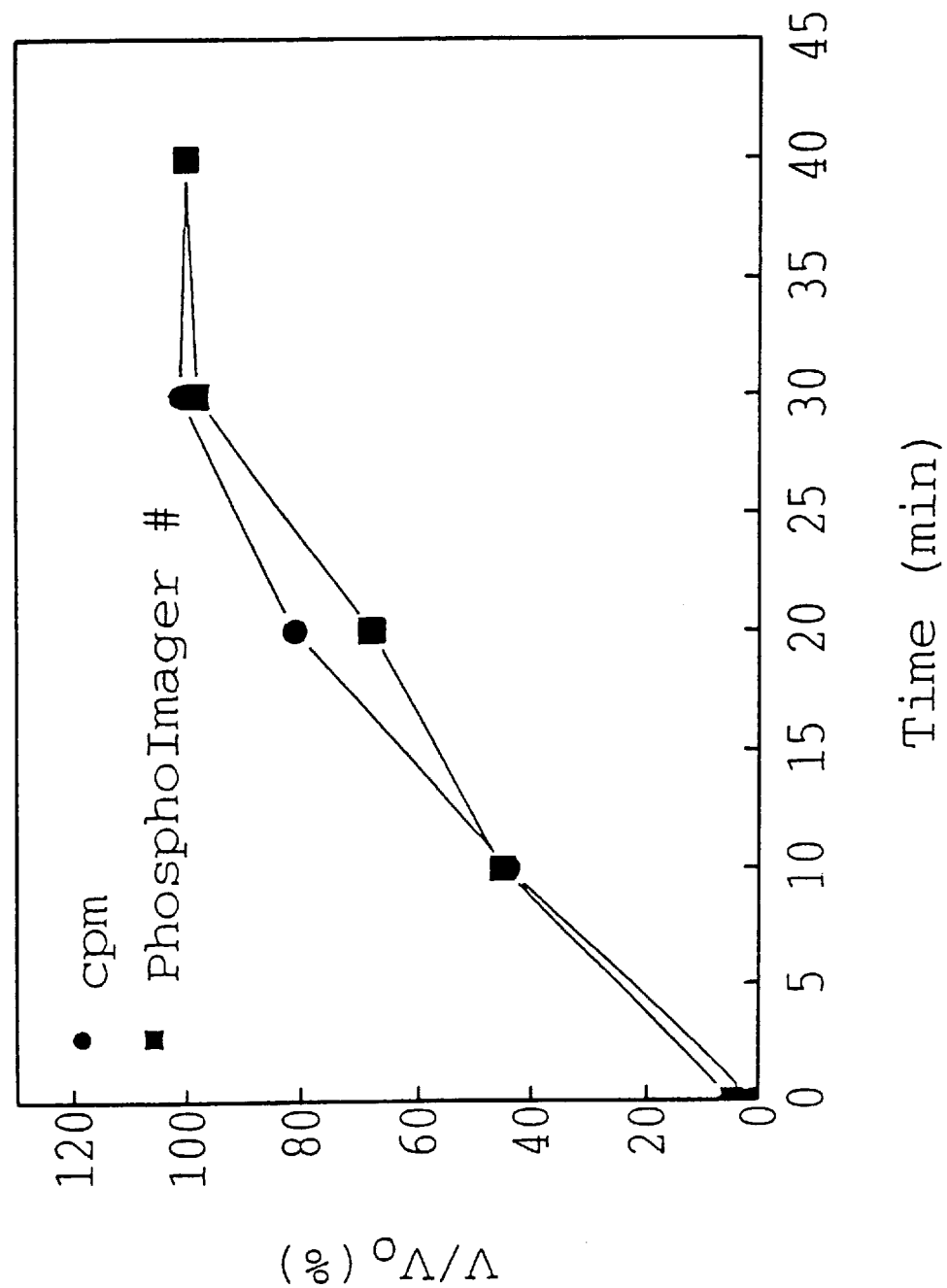
FIG. 4 illustrates the time course of phosphorylation of immobilized His-SpoOF; time (in minutes) is plotted against $v/v_0$ (%). Closed circles represent cpm, while closed squares represent Phospholmager #. The phosphorylation was carried out with 30 µl His-SpoOF resin (25%, v/v) per reaction, 1 µM KinA, and 400 µM ATP containing 2 µCi of [$\gamma$-$^{32}$P] ATP. The data are presented as relative activity to that at 40 min of the reaction.

FIG. 4 illustrates the time course of phosphorylation of immobilized His-SpoOF; time (in minutes) is plotted against $v/v_0$ (%). Closed circles represent cpm, while closed squares represent Phospholmager #. The phosphorylation was carried out with 30 μl His-SpoOF resin (25%, v/v) per reaction, 1 μM KinA, and 400 μM ATP containing 2 μCi of [γ-$^{32}$P] ATP. The data are presented as relative activity to that at 40 min of the reaction.

The rate of His-SpoOF phosphate formation was almost linear with time during the first 30 min. of the reaction and slowed down after 30 min. The same pattern of time course was observed with 100 $\mu$M ATP (data not shown).

The reproducibility of the above-described assay system was assessed by quantitating the amount of phosphorylated His-SpoOF from replicated samples within the same assay (intra-assay) and from independent assays (inter-assay). The results (see Table 2) showed that the standard deviations were 6.5% and 9.4% for intra-assay and inter-assay, respectively, under the conditions of 30 $\mu$l His-SpoOF resin, 1 $\mu$M KinA, and 100 $\mu$M ATP at 22° C. for 30 min.

TABLE 2

Assay Variation

| Intra-assay Experiments | SpoOF~P[1] (pmol) | S.D. (%) | n |
|---|---|---|---|
| 1 | 36 | 0.7 (1.9) | 3 |
| 2 | 32 | 2.1 (6.5) | 3 |
| 3 | 41 | 1.6 (3.9) | 3 |
| 4 | 34 | 1.3 (3.8) | 3 |
| Inter-assay | 36 | 3.4 (9.4) | 4 |

[1]The amount of SpoOF~P was calculated based on the cpm, the isotype dilution factor, and the specific activity of [$\gamma$-$^{32}$P]ATP.

Using the assay system described above, a semi-automated assay for histidine protein kinase was set up with an automated liquid handling system (MultiProbe, Packard, Meriden, Conn.) and with a 96-well filter plate system (MultiScreen, Millipore, Bedford, Mass.). The intra-assay variation of the semi-automated assay was within 10% (see Table 3) and the throughput was six to ten 96-well plates per operator per day. As noted previously, the systems described herein—including semi-automated assay systems and methods—may conveniently be used as disclosed herein to determine the inhibitory effect of various agents ("test samples") on the enzyme system being analyzed (e.g., histidine protein kinase).

TABLE 3

Intra-Assay Variation With Automated Liquid Handling System

| Experiment | Mean (cpm) | S.D. (%) | n |
|---|---|---|---|
| 1 | 2426 | 242 (10) | 30 |
| 2 | 1948 | 138 (7) | 96 |

Although the assay variation of the semi-automated assay was slightly higher than that of the manual assay, the throughput was much greater. Therefore, the semi-automated assay was suitable as a primary screen assay for inhibitors of histidine protein kinase.

Discussion

The method for determining histidine protein kinase activity described in this report is unique among all the available methods. The substrate, SpoOF, is immobilized onto a solid support via the histidine tag. A major advantage of this assay system is the quick separation of SpoOF from unreacted [$\gamma$-$^{32}$P]ATP, which is the rate-limiting step in determining the kinase activity when [$\gamma$-$^{32}$P]ATP is used. Another advantage of this assay system is the high affinity ($10^{-13}$) of the histidine tag to Ni-resin. The extra six histidine residues on SpoOF not only insure the binding of the SpoOF to the resin throughout the time course of the assay, they also provide an efficient one-step purification method for recombinant His-SpoOF expressed in *E. coli* cells.

The data presented herein shows that the radioactivity remaining on the resin after the phosphorylation reaction correlates very well with the amount of His-SpoOF phosphate formed during the reaction. Although the actual cpm value may vary from experiment to experiment due to isotope decay, the amount of His-SpoOF phosphate formed under the same assay conditions is reproducible. Therefore, the cpm values within the same experiment can be used directly to measure relative kinase activities of the samples.

The throughput of the assay described herein is remarkably and unexpectedly elevated over that of the conventional SDS-PAGE assay. With the use of an automated liquid handling system and 96-well filter plates, it is quite feasible to process six to ten plates a day, which is 480–960 reactions a day.

Taken together, the assay system described herein is suitable for high throughput screening of inhibitors of the histidine protein kinase. It is also contemplated that this assay be adapted for use with other proteins and enzymes, particularly with other protein kinases. As should be evident from the present disclosure, it is preferable that the substrate (e.g., kinase substrate) be fully active after the addition of a histidine tag or another appropriate tagging agent used to bind the substrate to the solid support (e.g. Ni-resin).

Moreover, while a high throughput system is preferred for use, as it is a more efficient and rapid means of identifying useful inhibitory agents, the systems described in the following Examples are also useful means of identifying new antibacterial, antimicrobial, and/or antibiotic agents.

Example 2

Autophosphorylation of Kinase A and Transphosphorylation of SpoOF

In order to analyze the effect of a potentially useful antibacterial or antibiotic compound or composition on the signal transduction process in bacteria, the inhibitory effect of such compounds on the sporulation operon proteins KinA and SpoOF may be examined essentially as follows. First, the following stock reagents were either prepared and used promptly or were stored at the indicated temperature:

8× salts: 2M KCl (5 mL); 1M MgCl$_2$ (800 mL); 1M CaCl$_2$ (100 mL); 10 mg/mL phenylmethylsulfonyl fluoride (200 mL); 1 M dithiothreitol (50 mL); 0.25M Na$_2$EDTA (32 mL) and H$_2$O (3.82 mL) (may be stored at −20° C.).

5× loading dye: 0.5 M TRIS-HCl, pH 6.8 (7.5 mL); 10% SDS (2 mL); 0.1% bromophenol blue (0.5 mL); 100% glycerol (3 mL); and 12.5M b-mercaptoethanol (0.3 mL).

1–1.3 mg/mL KinA: 15 mM TRIS-HCl, pH 8.0; 6 mM KCl; 4 mM b-mercaptoethanol; 40% glycerol (−20° C.).

1 mg/ml SpoOF: 17.5 mM TRIS-HCl, pH 8.0; 0.7 mM KCl; 0.7 mM MgCl$_2$; 0.7 mM CaCl$_2$; 5 mM b-mercaptoethanol; 30% glycerol (−20° C.).

5% stacking gel: 40% 29:1 acrylamide:bis acrylamide (1.25 mL); 0.5 M TRIS-HCl, pH 6.8 (2.5 mL); 10% SDS (0.1 mL); D-H$_2$O (6.15 mL); 10% ammonium persulfate (100 mL); and TEMED (25 mL).

SDS running buffer: TRIS-BASE (3.02 g, Sigma); glycine (14.4 g, Sigma).

SDS (1 g, Serva), D-H$_2$O (to 1 L).

The reaction mixture was prepared from 8× salts (87 mL); 1 M TRIS, pH 8 (87 mL); 50% glycerol (63 mL); 2% gelatin (31 mL); SpoOF (14.1 mL); and KinA (7.0 mL). Microcentrifuge tubes were filled with the reaction mixture (18.5 mL) as well as 1 mM solution of the test compound in DMSO (18.5 mL) and incubated for 15 minutes on ice. One hundred (100) mM [$^{32}$P]ATP/ATP solution (625 mCi, 3.0 mL) was added and the tubes were left for 10 minutes at room temperature. The reaction was then quenched with 5× loading dye (10 mL per tube) and the samples were either loaded on a prepared 5% stacking gel or stored on dry ice until ready for use. The prepared wells were filled with SDS running buffer, samples were loaded in the wells, and the upper buffer chamber was added and placed in a tank filed with SDS running buffer. Apply 80 volts (Hoeffer Unit) until the dye front reaches the bottom of the stacking gel and then increase the voltage to 250 volts until electrophoresis is complete.

If either enzyme is inhibited (which may be determined via its absence in the developed gel), an IC$_{50}$ is calculated by running predetermined inhibitor concentrations (e.g. 500, 250, 125, 62.5, 31.3, 15.7 and 7.9 mM). The percent inhibition is determined by measuring the concentration of radioactive phosphorus with a phosphoimager and calculating the values using a software program (e.g. Biorad Molecular Analyst, Biorad, Richmond, Calif.).

Example 3

Fatty Acid Inhibition of KinA Activity

A. Protein Purification

KinA was purified as described in Perego, et al., Id. (1989) and was confirmed to be approximately 80% pure as judged by Coomassie staining of acrylamide gels. SpoOF was purified from *E. coli* cells containing a derivative of the expression vector pKQB4 (Strauch, et al., *EMBO J.* 8: 1615–1621 (1989); Trach, et al., in *Genetics & Biotechnoloay of Bacilli*. Vol. 3, Zukowski, et al. (eds.), Academic Press, San Diego, pp. 357–365; Trach, et al., *Res. Microbiol.* 142: 815–823 (1991)). The purified SpoOF was determined to be homogeneous on the basis of high-performance liquid chromatography.

B. Chemicals and Fatty Acid Preparation

All chemicals and pure fatty acids were obtained from Sigma Chemical Company (St. Louis, Mo.). Fatty acids were routinely dissolved or resuspended in absolute ethanol to give 2% stock solutions which were stored at −20° C. in the dark. Although no decrease in inhibitory properties of solutions as old as three months has been observed, no solution of an unsaturated fatty acid over four weeks old was used and most solutions were used when they were less than one week old.

*B. subtilis* phospholipids were prepared from a 200 ml culture grown in LB to mid-logarithmic growth (approximately 2×10$^8$ cells/ml). The cells were centrifuged and the pellet resuspended in 4 ml of H$_2$O and divided in two. To each 2 ml aliquot, we added 2.5 ml chloroform and 5 ml methanol. The mixture was then centrifuged. The pellet was discarded and an additional 2.5 ml chloroform and 2.5 ml H$_2$O were added to the supernatant. The phases were separated by centrifugation and the lower phase was washed with 2M KCl and H$_2$O. The chloroform layer was siphoned off and dried under a stream of argon. The residue was resuspended in 1 ml ethanol and used as the total lipid extract.

To release fatty acids from the above-noted lipid extract, 0.5 ml of extract was made 0.5 M in KOH and heated for 2 hours at 65° C. in a sealed tube. Then, 5 ml of H$_2$O was added and the pH adjusted to 3.0 with HCl; at this pH, free fatty acids precipitate. One volume of ether was added next. The ether phase, which now contained the fatty acids, was washed twice with H$_2$O and dried under a stream of argon. The residue was resuspended in 1 ml ethanol and used as a fatty acid extract. The maximum of concentration of fatty acids in this preparation was estimated to be 3 mM based on the following assumptions: (1) 3×10$^{-14}$ g fatty acid per bacterial cell (Neidhardt, *E. coli and Salmonella typhimurim: Cellular and Molecular Biology*, Neidhardt (ed.), Am. Soc. for Microbiol., Washington, D.C., pp. 3–6 (1987); Scandella and Kornberg, *J. Bacteriol.* 98: 82–86 (1969); (2) 70% of the total cellular fatty acids were present in the phospholipid extract (Clejan, et al., *J. Bacteriol.* 168: 334–340 (1986)) and the recovery at each stage in the preparation was 100%; (3) the average molecular weight of a *B. subtilis* fatty acid is equal to 250 g/mole (Clejan, et al., Id. (1986)); and (4) total solubilization of the final dried residue. Since it was observed that total solubilization generally did not occur, it was surmised that the actual concentration was probably significantly less than 3 mM.

C. KinA Activity Assays

The reactions were performed in a 25 μl final volume containing 100 mM Tris pH 8.0, 100 mM KCl, 2 mM MgCl$_2$, 0.5 mM dithiothreitol, 10% (v/v) glycerol, 0.1 % (w/v) gelatin, 4% (v/v) ethanol, 200 μM total ATP containing approximately 1.5 μCi [gamma-$^{32}$P]ATP (New England Nuclear, 6000 Ci/mMol, 150 μCi/ml), 300 μM SpoOF protein and 0.04 μM KinA protein (Perego, et al., *J. Bacteriol.* 171: 6187–6196 (1989)) unless otherwise indicated. Fatty acids were added to varying final concentration from solutions made with 100% ethanol (the 4% ethanol concentration in the reaction mixture reflects these addition, or in the case of controls, the addition of ethanol alone). The reactions were initiated by addition of the ATP and incubated for thirty minutes at room temperature.

It was empirically determined that these conditions resulted in termination of the reaction during their linear phase and before reaching competition (data not shown). When higher KinA concentrations were used, the time of incubation was adjusted accordingly. The reactions were stopped by adding an equal volume of loading dye (0.25 M Tris pH 6.8, 20% (v/v) glycerol, 1% sodium dodecyl sulfate (w/v), 140 mM β-mercaptoethanol, 0.05% (w/v) bromophenol blue) and aliquots were loaded onto polyacrylamide gels (5% stacking, 15% separating, using the buffer system of Laemmi, Id., 1970).

The gels were run for approximately 16 hours at 10 mA constant current. The gels were covered with plastic wrap and subjected to autoradiography using Kodak XOmat RP1 film. Quantitation of activity was accomplished by cutting gels slices containing the appropriate phosphoprotein (usually SpoOF~P, see Section E below) and counting the Cerenkov radiation in a Beckman LF7500 scintillation counter (Beckman Instruments, Fullerton, Calif.). Equal-sized slices from blank areas of the gels were also counted and used to adjust for background. Percentage of activity was calculated using the value of the control reaction as 100%.

To determine if fatty acids served as a substrate for KinA-catalyzed phosphorylation, the following method was used. The above reaction conditions were employed except that no SpoOF was present; the KinA was at 2 μM and the reactions incubated for 5 minutes prior to the addition of fatty acids. After this initial incubation, to allow autophosphorylation to occur, 48 μl aliquots were added to tubes containing (a) two μl ethanol; (b) 2 μl of 2% oleic acid; and (c) 2 μl of 2% palmitic acid. The reactions were allowed to incubate 10 minutes after which time 0.5 ml H$_2$O and 0.5 ml heptane were added to each. After 10 minutes at room temperature, the phases were separated by centrifugation. The aqueous phases were washed with H$_2$O-saturated heptane and the heptane phases washed with heptane-saturated H$_2$O. The Cerenkov radiation in each phase and wash was determined.

D. Assay for Efficiency of Sporulation

The effect of ethanol upon the sporulation efficiency was tested by growing strains in 3 ml of Schaeffer's sporulation medium, with and without 0.7 M ethanol, for 24 hours at 37° C. (Schaeffer, et al., *PNAS USA* 54: 701–711 (1965)). Serial dilutions were then plated before and after treatment with CHCl$_3$ (10% v/v final, 10 minutes) in order to determine the total viable cell count and the spore count.

In the course of a search for agents which affect KinA activity, it has now been observed that a L-α-lysophosphatidylcholine preparation from egg yolk inhibits KinA phosphorylation of the SpoOF protein (data not shown). Various possible components of this heterogeneous mixture were tested to identify the specific inhibitory compound(s). L-α-phosphatidylcholine, L-α-glycerophosphatidylcholine, glycerophosphate, choline, L-α-phosphatidic acid (from egg yolk phosphatidylcholine) and the diacyl glycerols (and phosphocholine) produced by phospholipase C digestion of egg yolk L-α-phosphatidylcholine, stearic acid, palmitic acid, and oleic acid were tested at 0.08% final concentrations (data not shown). Only oleic acid and stearic acid were inhibitory, with oleic acid showing essentially complete inhibition and with stearic acid showing weak inhibition.

Twenty-eight different fatty acids were tested, including unsaturated, saturated and iso-branched fatty acids. Each one was qualitatively placed into one of three categories: inhibitors, weak inhibitors, and non-inhibitors; these qualitative assignments were later quantified, as discussed hereinbelow. Table 4 shows the classification of all the fatty acids tested.

TABLE 4

Fatty Acid Inhibitors of KinA Activity

| Systematic Name | Common Name | Formula |
|---|---|---|
| Inhibitors[a]: | | |
| cis-9-hexadecanoic | palmitoleic | 16:1 cis Δ 9 |
| cis-6-octadecanoic | petroselenic | 18:1 cis Δ 6 |
| cis-9-octadecanoic | oleic | 18:1 cis Δ 9 |
| cis-11-octadecanoic | cis-vaccenic | 18:1 cis Δ 11 |
| all cis-9,12,15-octadecanoic | linolenic | 18:3 cis Δ 9, 12, 15 |
| cis-11-eicosenoic | | 20:1 cis Δ 11 |
| all cis-5,8,11,14-eicosatetraenoic | arachidonic | 20:4 cis Δ 5, 8, 11, 14 |
| cis,cis-9,12-octadecenoic | linoleic | 18:2 cis Δ 9, 12 |
| Weak Inhibitors[b]: | | |
| 12-methyltridecanoic | isomyristic | iso 14:0 |
| 13-methyltetradecanoic | | iso 15:0 |
| octadecanoic | stearic | 18:0 |
| cis-9-tetradecenoic | myristoleic | 14:1 cis Δ 9 |
| Non-Inhibitory[c]: | | |
| trans-9-octadecenoic | elaidic | 18:1 trans Δ 9 |
| trans-11-octadecenoic | trans-vaccenic | 18:1 trans Δ 11 |
| trans-2-butenoic | crotonic | 41:1 trans Δ 2 |
| cis-13-docosenoic | erucic | 22:1 cis Δ 13 |
| cis-15-tetracosenoic | nervonic | 24:1 cis Δ 15 |
| 14-methylpentadecanoic | isopalmitic | iso 16:0 |

TABLE 4-continued

Fatty Acid Inhibitors of KinA Activity

| Systematic Name | Common Name | Formula |
|---|---|---|
| 15-methylhexadecanoic | | iso 17:0 |
| 16-methylheptadecanoic | isostearic | iso 18:0 |
| hexanoic | caproic | 6:0 |
| octanoic | caprylic | 8:0 |
| decanoic | capric | 10:0 |
| dodecanoic | lauric | 12:0 |
| tetradecanoic | myristic | 14:0 |
| hexadecanoic | palmitic | 16:0 |
| heptadecanoic | margaric | 17:0 |
| eicosanoic | arachidic | 20:0 |

[a] = Having $I_{0.5}$ values ≤ 70 μM
[b] = Having $I_{0.5}$ values of 100 μM to 500 μM
[c] = Unable to inhibit even when present at 1 mM or greater Data generated using the above-noted acids indicated that the stronger inhibitors had a chain length of 16–20 carbon atoms and at least one cis-unsaturated double bond within eleven carbon atoms of the carboxyl end (data not shown).

For example, in one study geared to determine the effect of four different C18 fatty acids on KinA activity, the KinA-catalyzed incorporation of $^{32}$P into the SpoOF protein was analyzed using four different fatty acids—oleic acid (18:1; cisΔ9); linolenic acid (18:3; cisΔ9, 12, 15); stearic acid (18:0); and elaidic acid (18:1; transΔ9). Each acid was used in experiments analyzing the effect of differing concentrations, as well. The concentrations used were (1) no fatty acid; (2) 2.5×10$^{31}$ $^3$M; (3) 6.3×10$^{-4}$M; (4) 2.5×10$^{-4}$M; (5) 6.3×10$^{-5}$M; (6) 2.5×10$^{-5}$M; (7) 6.3×10$^{-6}$M; and (8) 1.3×10$^{-6}$M. In all instances, the KinA concentration in the reactions was 0.04×10$^{-6}$M.

According to the results of the foregoing (data not shown), all of the stronger inhibitors had a chain length of 16–20 carbon atoms and at least one cis-unsaturated double bond within eleven carbon atoms of the carboxyl end. Isomers having the double bond in the trans configuration (e.g., elaidic, trans-vaccenic) were not inhibitory. None of the straight-chain saturated fatty acids tested was inhibitory, except for the weak inhibitor stearic acid. Of the five iso-branched species tested, the two with the shorter chain lengths (12-methyltridecanoic, 13-methyltetradecanoic) were weak inhibitors, while the three longer ones were not.

To quantify our initial assessment of inhibitory properties, the $I_{0.5}$ values (at 4×10$^{-8}$M KinA) were determined for each of the fatty acids. A representative determination is that for oleic acid. For example, the percent activity at an indicated oleic acid concentration is the ratio (×100) of the incorporation of $^{32}$P (from [γ$^{32}$P]ATP) into the SpoOF protein relative to the incorporation in the control reaction containing no inhibitor. Typically, data are gathered from at least two different experiments. The $I_{0.5}$ value is the concentration—e.g., the oleic acid concentration—corresponding to 50% activity as determined from the relevant graph.

We determined that the inhibitory strength (based on $I_{0.5}$ values) of the different fatty acids varied over two orders of magnitude (data not shown). If a cutoff of $I_{0.5}$=6×10$^{-5}$M is made, then the initial qualitative division of stronger from weaker inhibitors (see Table 4) is brought into agreement with the quantitative results.

Some interesting comparisons can be made which may relate to structural parameters necessary for efficient inhibition. Three of the cis-unsaturated fatty acids tested were not strong inhibitors (see Table 4). One of these fatty acids, cis-9-tetradecanoic, while having a cisΔ9 unsaturation, was only a weak inhibitor ($I_{0.5}=2\times10^{-4}$M. Since the C16 and C18 fatty acids having a cisΔ9 unsaturation were strong inhibitors, the weaker inhibition by cis-9-tetradecanoic (C14) may reflect a minimum chain length necessary for KinA inhibition. Similarly, the non-inhibitory properties of cis-13-docosenoic (C22) and cis-15-tetracosenoic (C24) may reflect the exceeding of a maximum chain length. Alternatively, their properties may be the result of the placement of their lone cis double bond beyond a maximally allowed distance from the carboxyl end (i.e., >11 carbons).

E. Analysis of Results

1 Inhibitory Fatty Acids Prevent Autophosphorylation of KinA.

The above-noted experiments were performed using a KinA concentration of $4\times1^{-8}$M. At this concentration, a band corresponding to KinA~P was not visible on the autoradiographs. Therefore, it could not be determined if the inhibition occurred at the KinA autophosphorylation step or at the phosphotransferase reaction between KinA~P and SpoOF. To address this question, assays were performed using a higher KinA concentration ($1\times10^{-6}$M). The prevention of stable autophosphorylation of KinA by oleic acid was confirmed. Data was gathered which verified the incorporation of $^{32}$P from [$\gamma^{32}$P]ATP into the KinA protein in the presence of SpoOF and differing concentrations of oleic acid (not shown). The assay was performed as disclosed hereinabove, except that the KinA concentration was increased to $1\times10^{-6}$M and the incubation time was shortened to three minutes.

It was observed that oleic acid inhibits the formation of KinA~P and SpoOF~P in a concentration-dependent fashion (data not shown). In experiments omitting SpoOF from the reaction, oleic acid showed similar concentration-dependent inhibition of KinA~P formation (data not shown).

These results indicate that oleic acid acts to inhibit the autophosphorylation of KinA. However, the continued presence of phosphorylated KinA even at the highest inhibitor concentration indicated that oleic acid can also inhibit the phosphotransfer from KinA~P to SpoOF.

2. Inhibition of KinA autophosphorylation is Not Competitive With ATP.

To determine the nature of the fatty acid inhibition of autophosphorylation, three series of reactions were performed. In the first series, no oleic acid was present; the second contained $2.5\times10^{-5}$M oleic acid; the third contained $7.0\times10^{-5}$M oleic acid. For each series, the ATP concentration in separate reactions was varied over the range of $2\times10^{-5}$ to $2\times10^{-3}$M (the Km for ATP is $1.3\times10^{-4}$M). Even at the lowest oleic acid concentration ($2.5\times10^{-5}$M) and highest ATP level ($2\times10^{-3}$M), the KinA was greater than 95% inhibited. These results indicate that ATP is not competitive with oleic acid inhibition.

3 3. Fatty Acids Do Not Promote Dephosphorylation of KinA~P.

The mechanism of fatty acid inhibition might result from either allosterically preventing KinA interaction with ATP or accelerated dephosphorylation of KinA~P. An accelerated loss of phosphate could conceivably occur by two different mechanisms:

(a) KinA~P+oleic→KinA+oleic-P, or

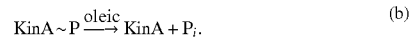

(b)

In (a), oleic acid serves as a substrate for the KinA enzyme and in (b), oleic acid acts as an allosteric enhancer of the autodephosphorylation reaction. (Note: in (a) and (b), the symbol "~" denotes a high-energy bond; and in (b), the symbol $P_i$ denotes inorganic phosphate.)

It was first determined that oleic acid did not serve as a substrate for KinA catalyzed phosphorylation. Oleic acid was added to a reaction mixture containing KinA~[$^{32}$P], and after a suitable incubation, the mixture was separated into organic and aqueous phases (as described above). Under the conditions used, fatty acid species would partition into the organic phase leaving the KinA~P and unincorporated [$\gamma^{32}$P]ATP in the aqueous phase. The amount of radioactivity in the organic phase containing oleic acid was negligible and no different from the amount present in the control reactions (data not shown).

Next, the ability of oleic acid to enhance the dephosphorylation of preformed KinA~P was investigated. Autophosphorylation of in the presence of [$\gamma^{32}$P]ATP was allowed to proceed for 60 minutes in the absence of SpoOF. At the end of this incubation, the reaction was divided into two aliquots, one receiving oleic acid to a final concentration of 2.5×10–4M. Samples from each were withdrawn at timed intervals, fractionated on polyacrylamide gels, the KinA bands excised and the incorporated radioactivity determined. There was no significant difference between the reactions in the loss of $^{32}$P from KinA~P (not shown). These results demonstrate that inhibitory fatty acids do not cause or accelerate the dephosphorylation of preformed KinA~P.

4. B. subtilis Phospholipids Contain Inhibitory Fatty Acids.

The majority of fatty acids found in B. subtilis have a branched chain structure and the amount of unsaturated varieties is low (Kaneda, Bacteriol. Rev. 41: 391–418 (1977); Kaneda, et at, Microbiol. Rev. 55: 288–302 (1991); Clejan, et al., Id. (1986)). To determine if a fatty acid with inhibitory properties towards KinA occurs in B. subtilis, a fatty acid extract was prepared as described above in section B of this Example. Thus, for example, we determined the extent of inhibition of KinA by B. subtilis fatty acids and a compound related to isostearic acid via KinA-catalyzed formation of SpoOF~P. In one such experiment, controls containing no inhibitor were run, as were samples including an 0.08% heterogeneous isostearic acid mixture (see section B above); 0.08% B. subtilis phospholipid extract; and 0.08% alcoholic-KOH-treated B. subtilis phospholipid extract.

When a total phospholipid preparation was used, there was no significant inhibition of KinA activity (data not shown). When these phospholipids were treated to release free fatty acids, the resulting fatty acid preparation inhibited the KinA activity by greater than 90% (not shown). These results demonstrate the occurrence in B. subtilis of at least one type of fatty acid that can inhibit the KinA enzyme. Furthermore, the inhibitory action is significantly reduced, or absent entirely, if the fatty acid(s) is esterified in the form of a phospholipid.

Of the inhibitors listed in Table 4, only two are definitely known to exist in B. subtills. These are 12-methyltridecanoic acid and 13-methyltetradecanoic acid. The former has been estimated to account for 1% of the fatty acids in total membrane lipid extracts, while the latter accounts for 15% (Clejan, et al., Id. (1986)). Both of these compounds are weak in vitro inhibitors of KinA and it is unlikely that either is responsible for the dramatic inhibition we observed. For example, using the value of 3 mM as the total fatty acid concentration of our preparation, then the 13-methyltetradecanoic concentration in it would be about $4.5\times10^{-4}$M. In our assay, this would be about $2\times10^{-5}$M 13-methyltetradecanoic, which is well below the $I_{0.5}$ value ($4\times10^{-4}$M) for this compound. The identification of the actual inhibitor(s) present remains under investigation.
5. Inhibition of Sporulation by Ethanol May Be Related to Fatty Acid Metabolism.

Two effects of sub-lethal ethanol concentrations on Bacillus are inhibition of sporulation and alterations in lipid and fatty acid metabolism. (See, e.g., Bohin, et al., *J. Bacteriol.* 127: 934–940 (1976); Kates, et al., *Can. J. Biochem. Physiol.* 40: 83–94 (1962); and Rigomier, et al., *J. Gen. Microbiol.* 121: 139–149 (1980).) The mechanism by which ethanol inhibits sporulation is not known, but certain mutations (e.g., ssa) in the SpoOA gene can overcome this defect (Bohin, et al., *J. Bacteriol.* 127: 934–940 (1982)). Other mutations in SpoOA, termed sof, can suppress SpoO defects caused by mutations in other components (e.g., SpoOF, SpoOB, kinA) of the phosphorelay system that governs the initiation of sporulation. (See, e.g., Kawamura, et al., *Mol. Gen. Genet*, 192: 189–193 (1983); Sharrock, et al., *Mol. Gen. Genet.* 194: 260–264 (1984); Shoji, et al., *J. Gen. Microbiol.* 134: 3249–3257 (1988); Spiegelman, et al., *J. Bacteriol.* 172: 5011–5019 (1990); Burbulys, et al., Id. (1991); and Trach, et al., Id. (1991).) These sof mutants can be divided into two classes: KinA-dependent and KinA-independent (Spiegelman, et al., Id. (1990)). If the ethanol effect on fatty acid metabolism is causally related to sporulation inhibition due to production of an inhibitor of KinA, it is reasonable to hypothesize that the KinA-dependent sof mutants would be sensitive to ethanol inhibition whereas the KinA-independent sof mutants would not. The effect of ethanol on the sporulation frequency of these types of sof mutants was then investigated.

The KinA-dependent sof-1 mutation does not completely alleviate the ethanol-induced sporulation inhibition, although it somewhat lessens the sensitivity compared to wild-type. In contrast, strains with the KinA-independent sof-4 mutation not only are resistant to ethanol inhibition, they actually sporulate better when ethanol is present (not shown). This latter phenomenon is particularly pronounced in a ΔSpoOF background where a 200-fold increase in sporulation frequency is seen. While these results cannot be considered proof that ethanol inhibits sporulation due to the synthesis or accumulation of a fatty acid inhibitor of KinA, they are consistent with this hypothesis.

6. Discussion.

The in vitro inhibition of KinA by fatty acids is unlikely to be the result of non-specific detergent effects for a number of reasons, including the fact that saturated fatty acids with short to medium chain length, and relatively strong detergent effects (e.g., caproic, caprylic, capric, lauric) are not inhibitors. Nor is it likely that the inhibition is somehow related to a sequestering of KinA (or other component) into a micelle structure; where known, the critical micelle concentration is well above the $I_{0.5}$ value of the stronger inhibitors (Mukerjee and Mysels, *National Standards Reference Data Service*, Vol. 36, National Bureau of Standards, Washington, D.C. (1971)). The inhibition would thus appear to be exerted by monomeric fatty acids—presumably, their $K^+$ salt form. However, in general, the fatty acids tested have free solubilities in the micromolar range, with critical micelle concentrations in the millimolar range. Little is known concerning the exact nature of the various lamellar and aggregate forms fatty acids assume in the 2–3 order of magnitude span between the two landmark concentration values. (See, e.g., Cistola, et al., *Biochemistry* 27: 1881–1888 (1988).) Since the $I_{0.5}$ values reported herein occur within that span, it is difficult to identify, with complete certainty, the structures in solution of the fatty acids that are responsible for the inhibition. This situation is not unique to our system; $K_a$ and $I_{0.5}$ values reported for fatty acid effects on other protein kinases fall within this "fuzzy" span of concentrations. (See, e.g., Buelt, et al., *J. Biol. Chem.* 266: 12266–12271 (1991); El Touny, et al., *J. Biol. Chem.* 265: 16437–16443 (1990); Murakami, et al., *J. Biol. Chem.* 261: 15424–15429 (1986); and Murakami, et al., *FEBS Letters* 192: 189–193 (1985).) In any event, the in vitro inhibitory levels of the fatty acids are concentration-dependent, and this is reflected in the $I_{0.5}$ values. The differing $I_{0.5}$ values obtained for individual fatty acid species must be related to specific chemical and physical features of the molecules that interact with KinA. An analysis of the similarities between these inhibitory fatty acids should provide clues as to the identity of a compound or compounds that serve as in vitro regulators.

The presence of at least one double bond in the cis conformation is a characteristic common to all of the fatty acids that were found to be strong inhibitors. This appears to be a very specific requirement in that isomers having a trans double bond were entirely non-inhibitory. Another requirement may be related to the positioning of the cis double bond in relation to the carboxyl end, although our data does not allow a definite conclusion on this point. The data also suggest that there may be somewhat stringent requirements concerning the chain length of the inhibitory cis-fatty acids, with those having 16 to 20 carbon atoms being better able to interact with KinA. The fact that two iso-branched saturated varieties (iso 14:0 and iso 15:0) have weak inhibitory properties may indicate that the actual in vivo inhibitor is a branched-chain cis-unsaturated species. However, this does not explain why the three longer iso-branched species (iso 16:0, iso 17:0, and iso 18:0) that were tested are not inhibitors.

The only straight-chain saturated fatty acid that showed any degree of inhibition was stearic acid. It was, in fact, a very weak inhibitor ($I_{0.5}=5\times10^{-4}$M). However, the stearic acid itself may not actually be inhibitory. When a heterogeneous mixture containing at least 20 different unidentified isomers and homologs of isostearic acid was tested, the evidence suggested that a very potent inhibitor ($I_{0.5}=2.5\times 10^{-6}$M or less) was present (see FIG. 4, lane 3). Perhaps the inhibitory properties of the stearic acid preparation assayed was due to the presence of minute traces of this unidentified inhibitor.

The actual presence of a KinA-inhibitory fatty acid in *B. subtilis* cells is indicated by our results showing that a fatty acid preparation from isoated phospholipids has inhibitory properties (see FIG. 4). The vast majority of fatty acids have a branched-chain structure (iso and anteiso types) and the proportion of unsaturated to saturated varieties is very low (Kaneda, *Bacteriol. Rev.* 41: 391–418 (1977); Kaneda, *Microbiol. Rev.* 55: 288–302 (1991); Clejan, et al., Id. (1986). Very little has been published concerning the types of unsaturated fatty acids found, although one report (Fulco, *J. Biol. Chem.* 244: 889–895 (1969)) indicates that a preferential position of unsaturation is Δ5. Other species of Bacilli have been shown to have fatty acids with double bonds in the Δ8, Δ9, or Δ10 positions (Fulco, Id.). A search of the literature has not uncovered a report specifically identifying any of the cis-unsaturated fatty acids listed in Table 4 as being present in *B. subtilis*. Branched-chain monounsaturated fatty acids have been detected in Bacillus species, including *B. subtilis*, but their chemical structure was apparently not analyzed further (see, e.g., Fulco, et al., *J. Biol. Chem.* 239: 998–1003 (1964 and Clejan, et al., Id. (1986)). Although it may be presumed that it is an actual fatty acid that is an in vivo inhibitor of KinA, an alternative possibility also exists. The inhibitor may not technically be a fatty acid, but rather some type of derivative such as an aliphatic alcohol, aldehyde, ketone, coenzyme A ester, or the like. At this time, the exact identity of the *B. subtilis* compound(s) responsible for KinA inhibition merits further study and experimentation.

Because it is an inhibitor of KinA, it is assumed that the fatty acid in question functions to prevent autophosphorylation of KinA during exponential growth. In some manner the metabolic signals indicating the end of vegetative growth and the onset of sporulation would be hypothesized to eliminate the inhibitory effect of the fatty acid. The KinA enzyme would then be autophosphorylated and thus begin the phosphorelay system that is required for sporulation initiation (Burbulys, et al., Id. (1991)). It is not known exactly how the inhibitory effect would be negated at this time. Among the possibilities are (a) the modification, degradation or lack of synthesis of the fatty acid inhibitor, or a combination of these; (b) the production of a non-inhibitory compound that can compete effectively with the inhibitor for the allosteric site on the KinA molecule; or (c) the production of an effector molecule that binds at a site distinct from that of the fatty acid and causes a conformational change in the KinA protein such that the inhibitory fatty acid is no longer able to bind.

Changes in the fatty acid and/or phospholipid profile during differentiation have been reported for a number of bacterial species including *B. subtilis*. (See, e.g., Bertsch, et al., *J. Bacteriol.* 98: 75–81 (1969); Bulla, et al., in *Spores VI*, Gerhardt, et al. (eds.), Am. Soc. for Microbiology, Washington, D.C., pp. 520–525 (1975); Heefner, et al., *J. Bacteriol.* 134: 38–47 (1978); Ishihara, et al., *Nippon Saikingaku Zasshi* 32: 703–707 (1977); Scandella, et al., Id. (1969); and Su, et al., *J. Bacteriol.* 134: 1434–1436 (1979).) Although sporulation in *B. subtilis* has been shown to be independent of gross changes in membrane fatty acid composition (Boudreaux, et al., *J. Bacteriol.* 148: 480–486 (1981)), specific changes during differentiation in the amount of a regulatory fatty acid, present at low concentration, cannot be ruled out. Our results (see, e.g., FIG. 4) showing that *B. subtilis* phospholipids do not inhibit KinA, whereas the free fatty acid preparation made from these lipids does inhibit, seem to indicate that a unesterified form of the inhibitory fatty acid present in an intracellular pool is responsible. Pools of unesterified fatty acids can occur in bacterial cells and, in fact, are unusually high in comparison to other organisms (O'Leary, *Bacteriol. Rev.* 26: 421–447 (1962)). The pool of free fatty acids in *B. subtilis* has been estimated to be about 2% under ordinary conditions (Mindich, *J. Bacteriol.* 110: 96–102 (1972)). However, the possibility that the inhibitory fatty acid esterified in a phospholipid may also play a regulatory role in vivo cannot be ruled out. It is possible that the context in which such a phospholipid is found—i.e., its association with other membrane components—could be a determining factor.

Sub-lethal concentrations of ethanol are known to cause major changes in the fatty acid composition of many bacteria, including Bacillus. (See, e.g., Ingram, et al., *Adv. Micribiol. Physiol.* 25: 26–47 (1984); Kates, et al., Id. (1962); and Rigomier, et al., *J. Gen. Micribiol.* 121: 139–149 (1980).) In *B. subtilis*, ethanol also prevents sporulation by turning wild-type cells into SpoOA phenocopies (Bohin, et al., *J. Bacteriol.* 127: 934–940 (1976); Bohin, et al., *J. Bacteriol.* 127: 934–940 (1982)). Our findings that KinA-independent SpoOA mutants are not sensitive to the Spo-ethanol effect are consistent with, but do not prove, a hypothesis that ethanol prevents sporulation because it results in the accumulation of a fatty acid that inhibits the autophosphorylation of KinA.

There has been at least one other line of investigation revealing that fatty acids can have effects upon the ability of bacilli to form spores. The inability to sporulate when grown upon certain complex organic medias is a well-known phenomenon. One type of antisporulation factor present in these media was identified as fatty acids (Foster, et al., *J. Bacteriol.* 59: 463–470 (1950); Hardwick , et al., *J. Bacteriol.* 61: 145–151 (1951)), and the antisporulation activity of some pure fatty acids was determined (Hardwick, et al., Id. (1951)). In general, it was found that saturated varieties were more potent than unsaturated ones, and that those of medium chain length (C10 to C14) were the most potent. Although these findings are diametric to our results showing C16–C20 cis-unsaturated fatty acids to be the inhibitors of KinA, it is difficult to compare the two types of experiments since it is not known what effects the exogenous addition of fatty acids has upon the intracellular composition.

Fatty acids are viable candidates for molecules playing a regulatory role in the "decision" to sporulate in *B. subtilis*. Perhaps analogous to the regulation of eukaryotic protein kinase C (for a review, see Bell and Burns, *J. Biol. Chem.* 266: 4661–4664 (1991)), fatty acids act as a second messenger transmitting environmental or metabolic information to a component of a signal transduction pathway, in this case the KinA enzyme of the *B. subtills* phosphorelay. Their role could be related to some aspect of intermediary metabolism that becomes altered as the cell depletes nutrients required for vegetative growth. Since fatty acids store a good deal of potential energy, they may function as energy state indicators. Being integral components of membrane lipids, they may serve to sense perturbations of membrane-associated metabolic events. It seems likely that the minor unsaturated fatty acids present in the cell are not randomly distributed in the cell membrane but rather are associated with specific structures or enzyme complexes with an essential spatial distribution. One example of such a complex would be the septation apparatus. Thus, the inhibition of KinA by a specific fatty acid could represent a growth-dependent signal emanating directly from a specific membrane-associated complex.

The foregoing specification, including the specific embodiments and examples, is intended to be illustrative of the present invention and is not to be taken as limiting. Numerous other variations and modifications can be effected without departing from the spirit and scope of the present invention.

We claim:

1. An novel assay method for use in identifying novel antibiotic, antibacterial, or antimicrobial agents, comprising:
   a. affixing a substrate onto a solid support;
   b. admixing said solid support-affixed substrate with a sensor protein and a test sample;
   c. allowing said admixture to incubate for a predetermined period of time;
   d. separating said solid support from the remainder of said admixture; and
   e. examining said solid support to determine whether a reaction product is present, thereby determining the therapeutic potential of said test sample.

2. The method of claim 1, wherein said sensor protein is an enzyme or a catalytically active portion thereof.

3. The method of claim 2, wherein said enzyme is a kinase enzyme or an enzymatically active polypeptide portion thereof.

4. The method of claim 3, wherein said kinase is histidine protein kinase.

5. The method of claim 3, wherein said admixture further includes a high-energy phosphate source.

6. The method of claim 5, wherein said high-energy phosphate source is ATP or GTP.

7. The method of claim 5, wherein said high-energy phosphate source is labeled.

8. The method of claim 1, wherein said substrate comprises a bacterial protein or polypeptide molecule.

9. The method of claim 1, wherein said substrate comprises a bacterial SpoOF protein or a polypeptide portion thereof.

10. The method of claim 1, wherein said substrate further comprises a linker.

11. The method of claim 10, wherein said linker comprises one or more histidine residues.

12. The method of claim 1, wherein said solid support comprises a resin.

13. The method of claim 12, wherein said resin is a nickel-conjugated exchange resin (Ni-resin).

14. A method for identifying antibiotic, antibacterial or antimicrobial agents, comprising:
   a. admixing a substrate with a kinase enzyme, a high-energy phosphate source, and a test sample;
   b. allowing said admixture to incubate for a predetermined period of time;
   c. separating any reaction product formed in step b from the remainder of said admixture; and
   d. ascertaining the amount of reaction product formed, thereby determining the therapeutic potential of said test sample.

15. The method of claim 14, wherein said substrate or said enzyme is labeled.

16. The method of claim 14, wherein said determining step comprises using a labeled antibody which forms a labeled immunocomplex with a substrate or an enzyme, and then quantitating the amount of labeled immunocomplex formed.

17. The method of claim 15 or 16, wherein said label comprises a fluorescent label, a radioactive label, biotin, or the like.

18. The method of claim 14, wherein said substrate is affixed to a solid support.

19. The method of claim 18, wherein said solid support comprises a resin.

20. The method of claim 19, wherein said resin is a nickel-conjugated exchange resin (Ni-resin).

21. The method of claim 14, wherein said high-energy phosphate source is ATP or GTP.

22. The method of claim 14, wherein said enzyme comprises a kinase enzyme or a polypeptide having an amino acid residue sequence corresponding to that of a sequential subset of the amino acid residue sequence of said enzyme.

23. The method of claim 22, wherein said kinase is histidine protein kinase.

24. The method of claim 14, wherein said substrate comprises a bacterial protein or polypeptide molecule.

25. A high-throughput assay system or kit comprising the following reagents:
   a. a substrate affixed to a solid support;
   b. a sensor protein; and
   c. a high-energy phosphate source, each in an amount sufficient to conduct at least one assay.

26. The assay system of claim 25, wherein one or more of said reagents is labeled.

27. The assay system of claim 25, wherein each of said reagents is in a separate container.

28. The assay system of claim 27, wherein said containers are enclosed in a package, which package further includes instructions for use of said reagents.

29. The assay system of claim 25, wherein said sensor protein comprises an enzyme or a catalytically active portion thereof.

30. The assay system of claim 25, wherein said high-energy phosphate source is ATP or GTP.

31. The assay system of claim 25, wherein said enzyme comprises a kinase enzyme.

32. The assay system of claim 30, wherein said kinase is histidine protein kinase.

33. The assay system of claim 25, wherein said substrate comprises a bacterial protein or polypeptide molecule.

34. The assay system of claim 32, wherein said substrate comprises a SpoOF protein or a polypeptide portion thereof.

35. The assay system of claim 32, wherein said substrate further includes a linker.

36. The assay system of claim 34, wherein said linker comprises one or more histidine residues attached to said substrate.

37. The assay system of claim 25, wherein said solid support comprises a resin.

38. The assay system of claim 36, wherein said resin is a Ni-resin.

* * * * *

UNITED STATES PATENT AND TRADEMARK OFFICE
CERTIFICATE OF CORRECTION

PATENT NO : 6,043,045
DATED : March 28, 2000
INVENTOR(S) : Hoch, et al.

It is certified that error appears in the above-identified patent and that said Letters Patent are hereby corrected as shown below:

In Column 1, line 7, please insert:

--This invention was made with government support under Contract Nos. GM19146 and CA11778 by the National Institutes of Health. The government has certain rights in the invention.--

Signed and Sealed this

Twenty-fourth Day of April, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.    : 6,043,045
DATED         : March 28, 2000
INVENTOR(S)   : Hoch et al.

It is certified that error appears in the above-identified patent and that said Letters Patent is hereby corrected as shown below:

Title page,
Item [63], Related U.S. Application Data, the entire paragraph should read as follows:

-- Continuation-in-part of application No. 08/528,737, Sep. 15, 1995, Pat. No. 5,747,276. --

Column 1,
Line 4, should read as follows:

-- This application is an International 371 of PCT/US96/14652 filed Sep. 12, 1996 and a continuation-in-part of Ser. No. 08/528,737 filed Sep. 15, 1995, U.S. Pat. No. 5,747,276. --

Signed and Sealed this

Tenth Day of June, 2003

JAMES E. ROGAN
*Director of the United States Patent and Trademark Office*